(12) United States Patent
Hontz et al.

(10) Patent No.: US 11,672,535 B2
(45) Date of Patent: Jun. 13, 2023

(54) CARTRIDGE BASED LOCKOUT MECHANISM FOR RIGHT ANGLE SURGICAL STAPLER

(71) Applicant: Cilag GmbH International, Zug (CH)

(72) Inventors: Jesse L. Hontz, Cincinnati, OH (US); Jason M. Rector, Maineville, OH (US); Nicholas Fanelli, Morrow, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/718,784

(22) Filed: Apr. 12, 2022

(65) Prior Publication Data
US 2022/0296239 A1 Sep. 22, 2022

Related U.S. Application Data

(62) Division of application No. 16/395,359, filed on Apr. 26, 2019, now Pat. No. 11,324,504.

(51) Int. Cl.
*A61B 17/072* (2006.01)
(52) U.S. Cl.
CPC ............ *A61B 17/07207* (2013.01); *A61B 2017/07271* (2013.01); *A61B 2017/07278* (2013.01); *A61B 2017/07285* (2013.01)
(58) Field of Classification Search
CPC .... A61B 17/07207; A61B 2017/07271; A61B 2017/07278; A61B 2017/07285
USPC ............................................ 227/175.2–175.4
See application file for complete search history.

(56) References Cited

U.S. PATENT DOCUMENTS

| | | | | |
|---|---|---|---|---|
| 5,240,163 | A * | 8/1993 | Stein | A61B 17/072 227/175.3 |
| 9,668,729 | B2 * | 6/2017 | Williams | A61B 17/068 |
| 9,949,788 | B2 * | 4/2018 | Boudreaux | A61B 18/1445 |
| 10,485,542 | B2 * | 11/2019 | Shelton, IV | A61B 17/0686 |
| 2005/0139632 | A1 * | 6/2005 | Schwemberger | A61B 17/072 227/19 |
| 2006/0000868 | A1 * | 1/2006 | Shelton | A61B 17/07207 227/175.1 |
| 2007/0029364 | A1 * | 2/2007 | Kruszynski | A61B 17/072 227/175.2 |
| 2014/0291382 | A1 * | 10/2014 | Lloyd | A61B 17/07207 227/176.1 |
| 2016/0220266 | A1 * | 8/2016 | Shelton, IV | A61B 17/105 |
| 2016/0249914 | A1 * | 9/2016 | Zhang | A61B 17/295 227/175.3 |

(Continued)

*Primary Examiner* — Dariush Seif
(74) *Attorney, Agent, or Firm* — Frost Brown Todd LLP

(57) ABSTRACT

A surgical stapler includes a body, a shaft assembly, and an end effector configured to receive a staple cartridge. The end effector is actuatable between an open state for receiving tissue and a closed state for clamping the tissue. A closure system operatively coupled with the end effector is operable to actuate the end effector from the open state to the closed state. A firing system operatively coupled with the end effector is actuatable to fire the end effector to staple and cut the clamped tissue. A lockout member operatively coupled with the closure system and the firing system is configured to inhibit actuation of the closure system to prevent closure of the end effector when an unspent staple cartridge is absent from the end effector. The lockout member is also configured to inhibit actuation of the firing system to prevent repeated firing with the same staple cartridge.

20 Claims, 35 Drawing Sheets

(56) References Cited

U.S. PATENT DOCUMENTS

| | | | |
|---|---|---|---|
| 2016/0249945 A1* | 9/2016 | Shelton, IV | A61B 17/068 606/171 |
| 2017/0143336 A1* | 5/2017 | Shah | A61B 17/07207 |
| 2017/0224339 A1* | 8/2017 | Huang | A61B 17/295 |
| 2017/0281155 A1* | 10/2017 | Shelton, IV | A61B 17/068 |
| 2017/0281177 A1* | 10/2017 | Harris | A61B 17/1155 |
| 2017/0290584 A1* | 10/2017 | Jasemian | A61B 17/07207 |
| 2020/0337700 A1* | 10/2020 | Hontz | A61B 17/07207 |

* cited by examiner

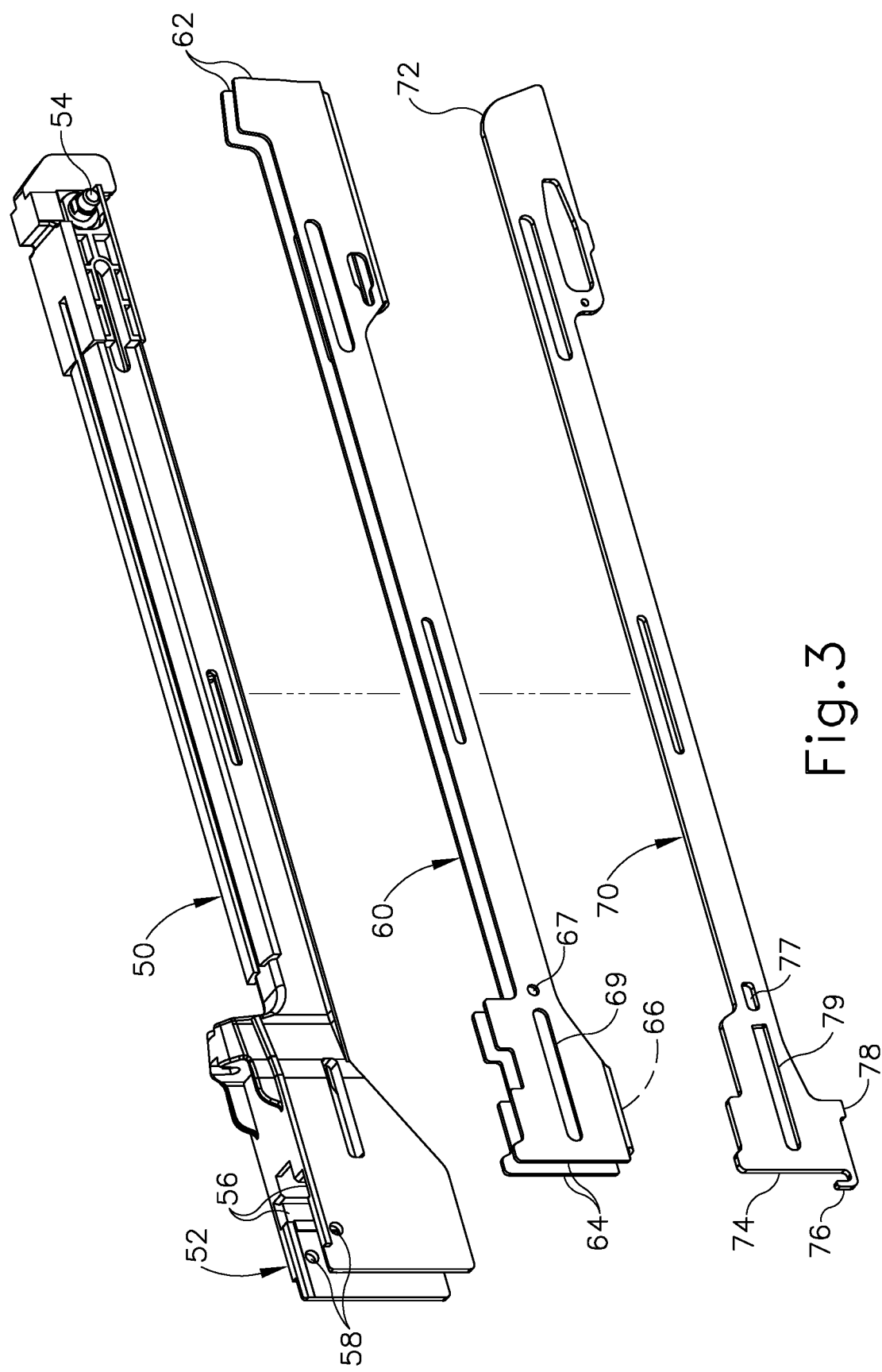

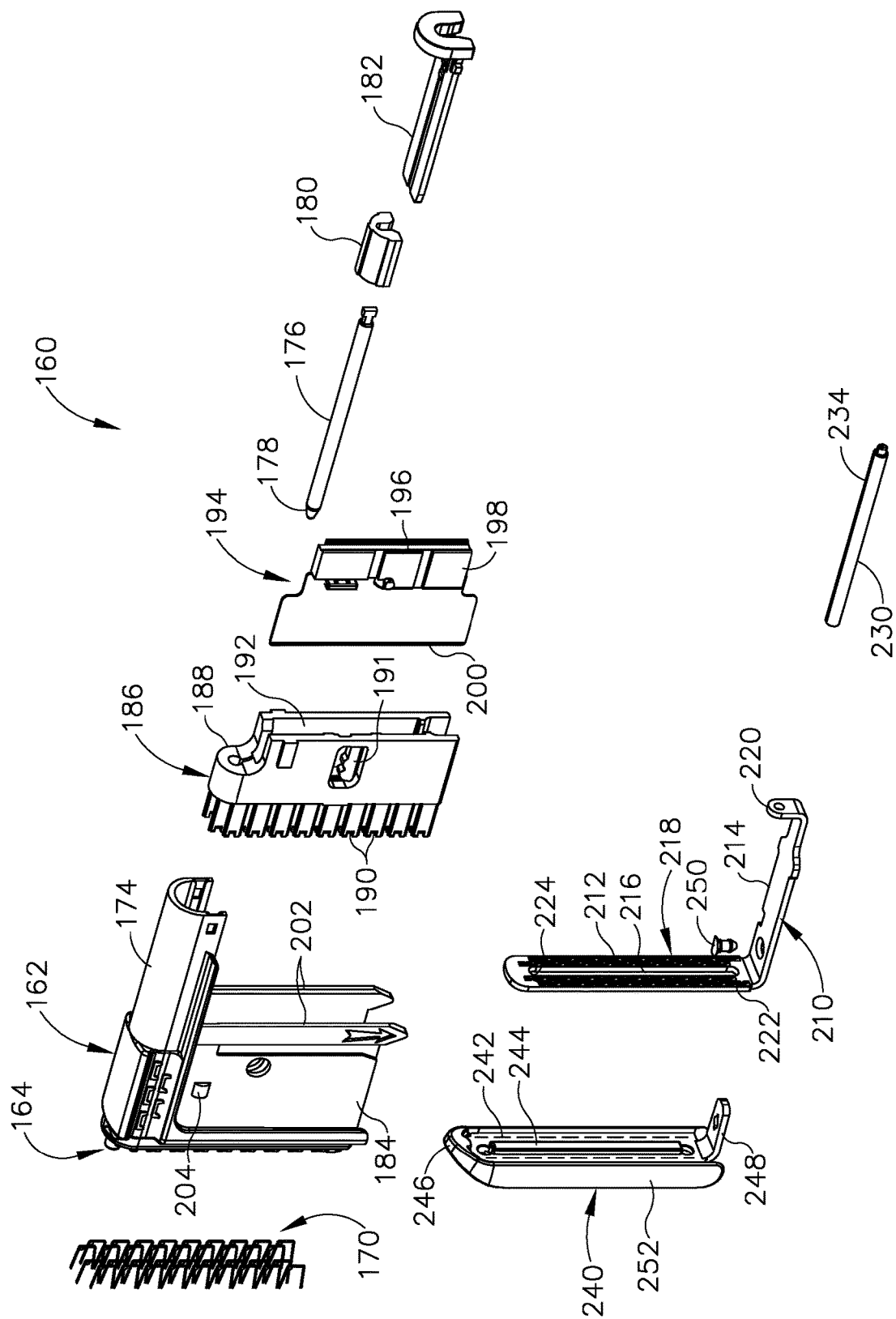

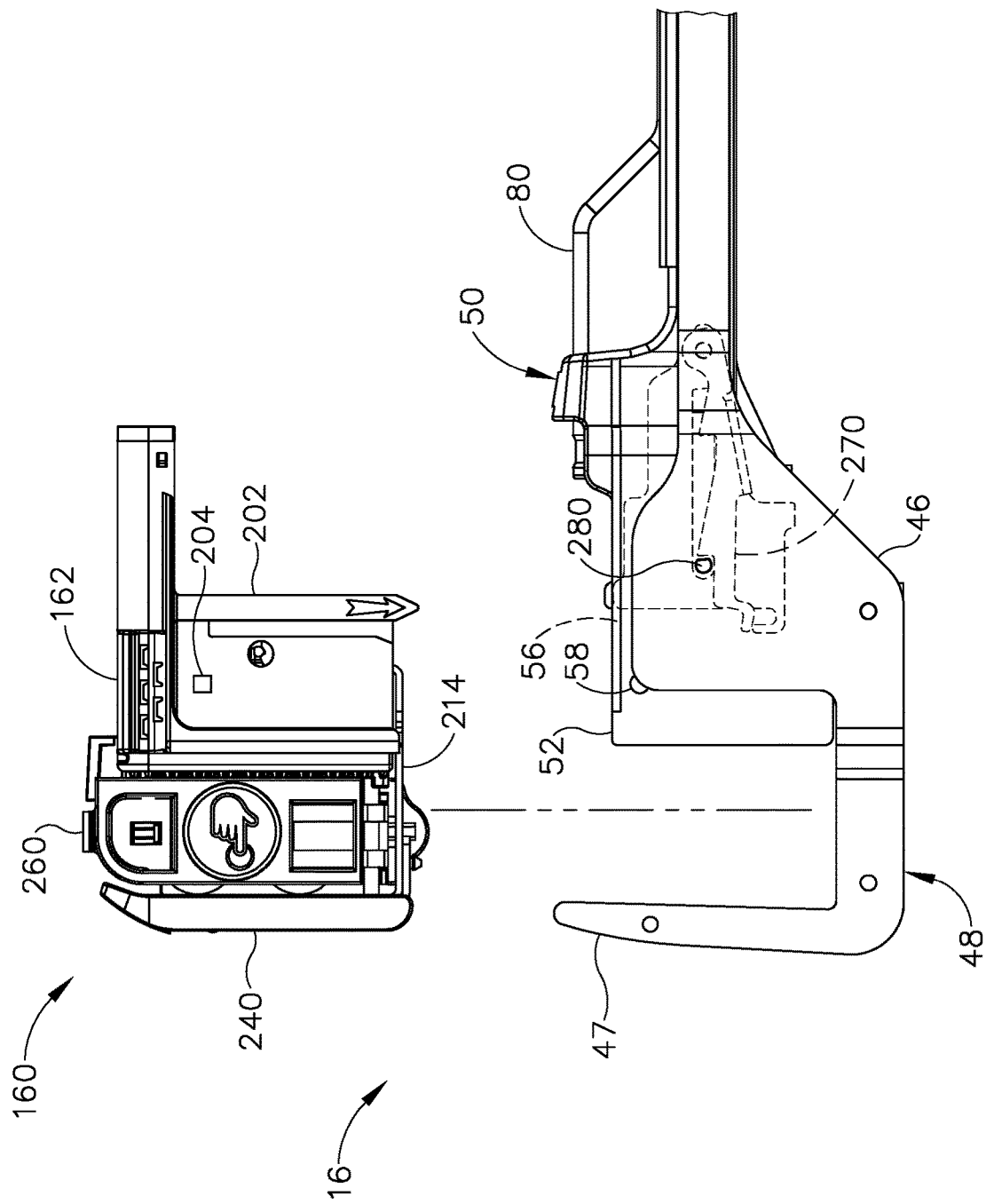

CARTRIDGE BASED LOCKOUT MECHANISM FOR RIGHT ANGLE SURGICAL STAPLER

This application is a divisional of U.S. patent application Ser. No. 16/395,359, entitled "Cartridge Based Lockout Mechanism for Right Angle Surgical Stapler," filed Apr. 26, 2019 and issued as U.S. Pat. No. 11,324,504 on May 10, 2022.

BACKGROUND

Some surgical staplers are operable to clamp down on one or more layers of patient tissue, form staples through the layers of tissue to substantially seal the layers of tissue together near the formed staples, and cut through the layers of clamped tissue for forming severed ends of operatively sealed tissue. An exemplary stapling instrument includes a pair of cooperating elongate jaw members, where each jaw member is adapted to be inserted into a patient and positioned relative to tissue that is to be stapled. One of the jaw members supports a staple cartridge having at least two laterally spaced rows of staples contained therein, and the other jaw member supports an anvil having staple-forming pockets configured to align with the rows of staples in the staple cartridge. Generally, the stapling instrument further includes one or more pusher bars that are actuatable relative to the jaw members to drive staples from the staple cartridge, through tissue clamped between the jaw members, and against the anvil for forming, and also to drive a knife member through the clamped tissue and thereby cut the tissue simultaneously with or subsequent to the stapling. In this manner, the stapling instrument is operable to form a plurality of laterally spaced rows of deformed staples in the clamped tissue, where such rows may comprise linear rows and/or arcuate rows. The knife blade may cut the tissue along a linear or arcuate path that extends between adjacent rows of the staples formed in the clamped tissue.

Merely exemplary surgical staplers are disclosed in U.S. Pat. No. 5,605,272, entitled "Trigger Mechanism for Surgical Instruments," issued Feb. 25, 1997; U.S. Pat. No. 5,697,543, entitled "Linear Stapler with Improved Firing Stroke," issued Dec. 16, 1997; U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007; and U.S. Pat. No. 10,045,780, entitled "Method of Applying Staples in Lower Anterior Bowel Resection," issued Aug. 14, 2018. The disclosure of each of the above-cited U.S. patents and U.S. patent publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3 depicts a disassembled perspective view of actuatable components of the shaft assembly of the surgical stapler of FIG. 1A, including a closure bar of the closure system, a staple bar of the firing system, and a knife bar of the firing system;

FIG. 8 depicts a disassembled perspective view of the staple cartridge unit of the surgical stapler of FIG. 1A;

FIG. 9A depicts a side elevational view of the end effector of the surgical stapler of FIG. 1A, showing a lockout member of the end effector in a lockout position when a staple cartridge unit is absent from the distal support structure;

Figure 1A:
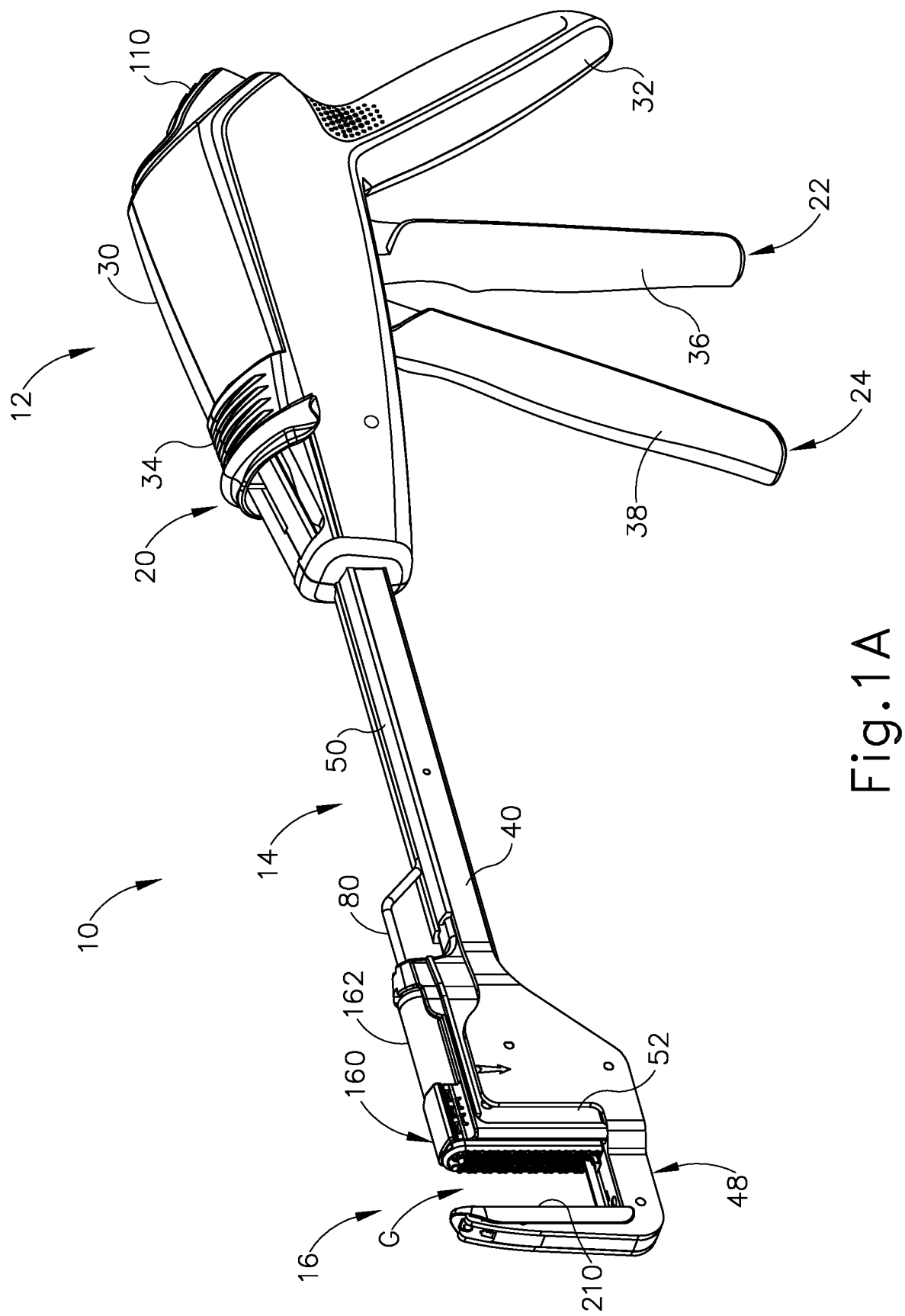
FIG. 1A depicts a perspective view of an exemplary surgical stapler having a handle assembly, a shaft assembly, and an end effector, showing a tissue retaining pin actuation system in a retracted position and the end effector in an open state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," "left," "right" or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about," "approximately," and the like in connection with any numerical values or ranges of values are intended to encompass the exact value(s) referenced, as well as a suitable dimensional tolerance that enables the referenced feature or combination of features to function for the intended purpose described herein.

I. Overview of Exemplary Right Angle Surgical Stapler

FIG. 1A depicts an exemplary right angle linear surgical stapler (10) that is configured to staple and cut tissue in various non-endoscopic ("open") surgical procedures, including colorectal, thoracic, and bariatric procedures, for example. Right angle linear surgical stapler (10) (also referred to as a "right angle linear cutter") generally includes a handle assembly (12), a shaft assembly (14) extending distally from handle assembly (12), and an end effector (16) at a distal end of shaft assembly (14). As described below, end effector (16) is provided with a "right angle" configuration such that end effector (16) clamps, staples, and cuts tissue in a plane that extends transversely at a right angle to a longitudinal axis defined by shaft assembly (14).

As described in greater detail below, surgical stapler (10) includes several actuation systems for operating end effector (16) via handle assembly (12) during a surgical procedure on a patient. In particular, surgical stapler (10) includes a tissue retaining pin actuation system (20) operable to initially retain tissue within end effector (16); a closure system (22) operable to clamp tissue with end effector (16); and a firing system (24) operable to subsequently staple and cut tissue with end effector (16).

While the teachings herein are shown and described in the context of a "linear" surgical stapler (10) configured to apply linear rows of staples and a linear cut line in tissue, it will be appreciated that any one or more of the teachings herein may be applied to a surgical stapler configured to apply staple rows and a tissue cut line with a non-linear (e.g., curved) configuration, such as a surgical stapler of the type disclosed in any one or more of the references incorporated by reference herein.

A. Handle Assembly and Shaft Assembly of Surgical Stapler

Figure 1B:
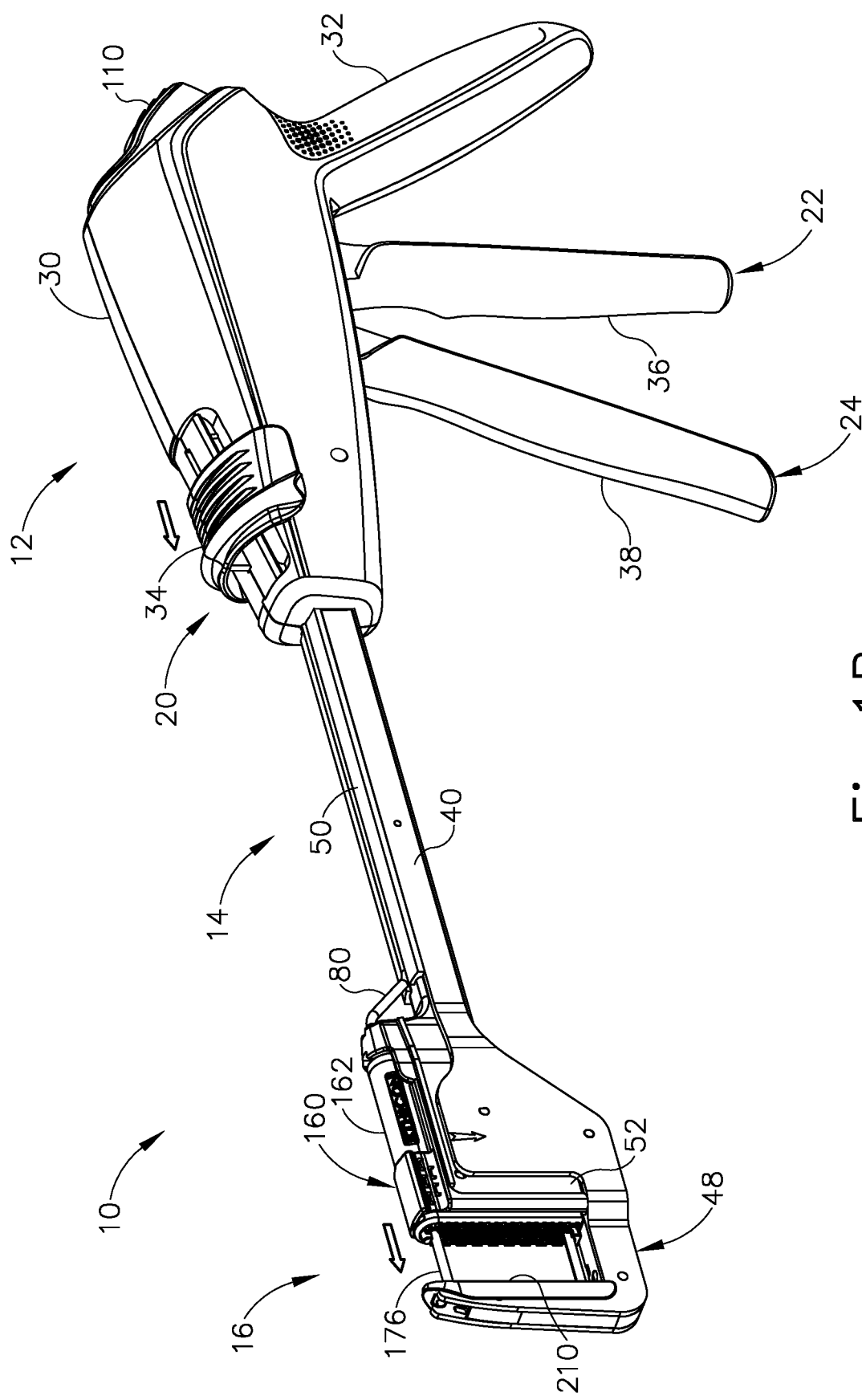
FIG. 1B depicts a perspective view of the surgical stapler of FIG. 1A, showing the tissue retaining pin actuation system in an extended position while the end effector remains in the open state.
Figure 1C:
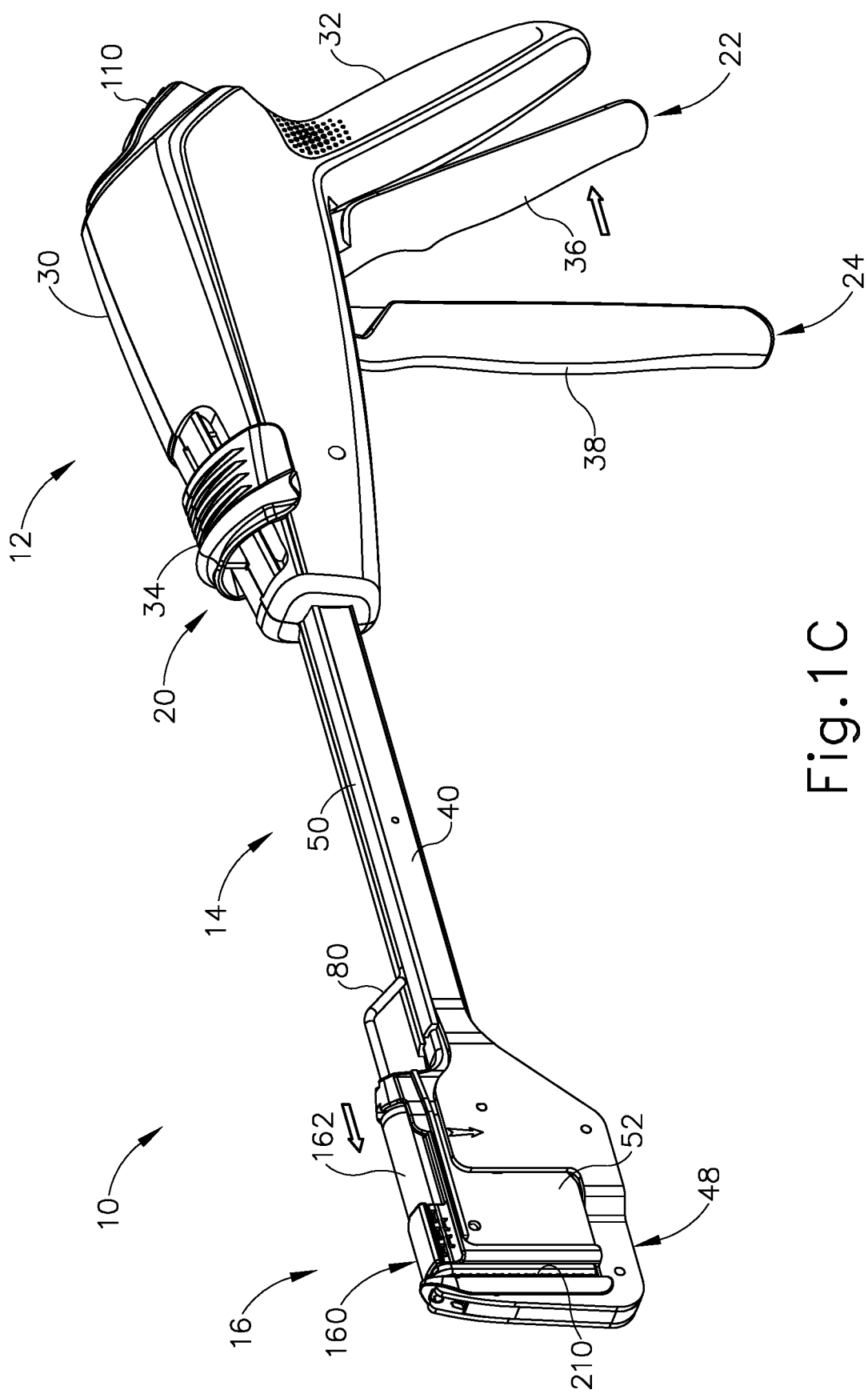
FIG. 1C depicts a perspective view of the surgical stapler of FIG. 1A, showing the end effector in a closed state via actuation of a closure system, while the tissue retaining pin actuation system remains in the extended position.
Figure 1D:
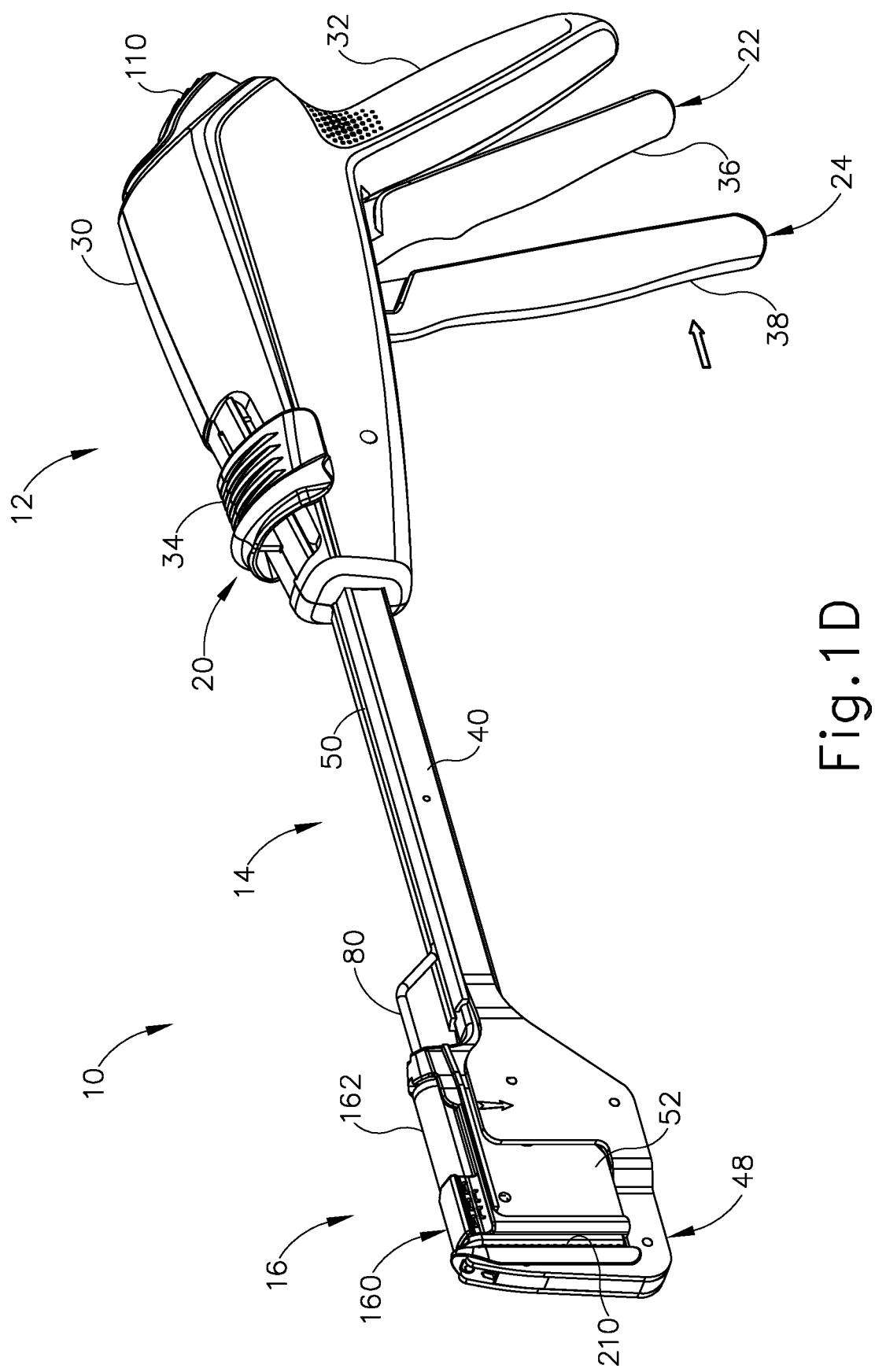
FIG. 1D depicts a perspective view of the surgical stapler of FIG. 1A, showing the end effector in a fired state via actuation of a firing system to effect stapling and cutting of tissue captured by the end effector, while the tissue retaining pin actuation system remains in the extended position.

As shown in FIG. 1A, handle assembly (12) includes a housing (30) that defines a pistol grip (32), a saddle shaped slide (34) slidably disposed on an upper portion of handle housing (30), a pivotable closure trigger (36), and a pivotable firing trigger (38). Closure trigger (36) and firing trigger (38) are operatively coupled with end effector (16) via shaft assembly (14) such that end effector (16) is configured to close and thereby clamp tissue in response to actuation of closure trigger (36), and subsequently staple and cut tissue (i.e., "fire") in response to actuation of firing trigger (38). FIG. 1A shows slide (34) and closure trigger (36) in unactuated configurations such that end effector (16) is configured to receive tissue laterally within a gap (G) (or "aperture") defined between a cartridge housing (162) and an anvil (210) of a replaceable staple cartridge unit (160) (or "reload") mounted within end effector (16). As shown in FIG. 1B, translating slide (34) distally toward end effector (16) extends a tissue retaining pin (176) of staple cartridge unit (160) distally for capturing the tissue between anvil (210) and cartridge housing (162). As shown in FIG. 1C, subsequently actuating closure trigger (36) toward pistol grip (32) drives cartridge housing (162) distally toward anvil (210), thereby clamping tissue therebetween. As shown in FIG. 1D, subsequently actuating firing trigger (38) toward pistol grip (32) drives staples distally into the clamped tissue and also cuts the tissue between formed staple lines with a knife member (194) (see FIG. 8), as described in greater detail below.

Figure 2:
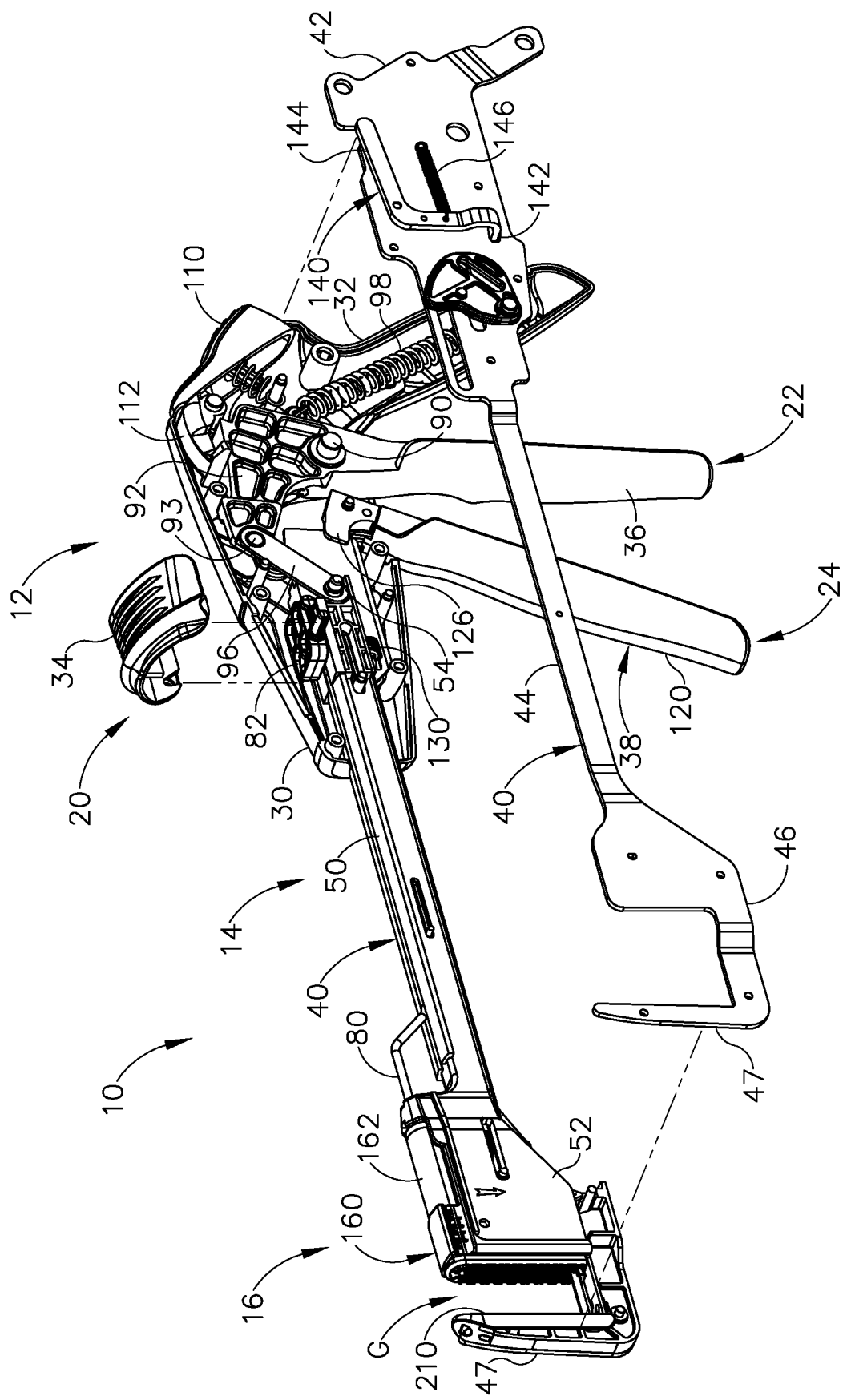
FIG. 2 depicts a partially disassembled perspective view of the surgical stapler of FIG. 1A.

As shown in FIG. 2, surgical stapler (10) includes a pair of longitudinally extending side plates (40) that cooperate to define a frame structure of stapler (10) that supports tissue retaining pin actuation system (20), closure system (22), and firing system (24). Each side plate (40) includes a proximal frame portion (42) housed within handle housing (30); a medial shaft portion (44) that defines a respective outer lateral side of shaft assembly (14); and a distal jaw portion (46) having an upwardly extending distal hook (47). Distal jaw portions (46) cooperate with the distal end of a closure bar (50), described below, to define a U-shaped distal support structure (48) of end effector (16) that removably receives staple cartridge unit (160). As used herein, the term "U-shaped" refers to the shape presented by end effector (16) in any of the side elevational views depicted herein.

As shown in FIG. 3, slidably disposed between and supported by side plates (40) are elongate actuatable components of actuation systems (20, 22, 24), which operatively couple handle assembly (12) with staple cartridge unit (160); including a closure bar (50), a staple bar (60), and a knife bar (70). Closure bar (50) includes a cartridge-receiving distal portion (52) configured to receive and support staple cartridge unit (160). Closure bar (50) and staple bar (60) are each configured as a double-sided structure having first and second lateral sides spaced apart from one another, and an inner channel extending longitudinally therebetween. This configuration enables an arrangement of shaft assembly (14) in which knife bar (70) is nested and slidably disposed within the longitudinal inner channel of staple bar (60), and in which staple bar (60) in turn is nested and slidably disposed within the longitudinal inner channel of closure bar (50). Moreover, staple bar (60) and knife bar (70) are longitudinally translatable independently of closure bar (50) through a range of longitudinal motion that enables independent closure and firing of end effector (16). As described in greater detail below, closure bar (50) is operable to actuate cartridge housing (162) longitudinally relative to anvil (210) for clamping tissue in response to actuation of closure trigger (36). Staple bar (60) is operable to actuate a staple driver member (186) (see FIG. 8) longitudinally relative to cartridge housing (162) for stapling the clamped tissue. Knife bar (70) is operable to actuate knife member (194) (see FIG. 8) longitudinally relative to cartridge housing (162) and staple driver member (186) for cutting the clamped tissue.

Tissue retaining pin actuation system (20) of surgical stapler (10) includes slide (34) of handle assembly (12), tissue retaining pin (176) of staple cartridge unit (160), an elongate pushrod (80) extending longitudinally along an upper side of shaft assembly (14), and a pushrod driver (82) slidably disposed within handle assembly (12). A distal end of pushrod (80) is configured to releasably couple with tissue retaining pin (176) upon insertion of staple cartridge unit (160) into distal support structure (48) of end effector (16). A proximal end of pushrod (80) is coupled with pushrod driver (82), which in turn is coupled with slide (34). Accordingly, longitudinal translation of slide (34) between proximal and distal positions drives longitudinal translation of tissue retaining pin (176) relative to cartridge housing (162) between retracted and extended positions. As shown in FIG. 1A, tissue retaining pin (176) is configured to assume a retracted position in which retaining pin (176) is housed within cartridge housing (162) when slide (34) is in a proximal position. As shown in FIG. 1B, tissue retaining pin (176) is configured to assume an extended position in which a distal end of retaining pin (176) engages anvil (210), thereby retaining tissue positioned within gap (G) of staple cartridge unit (160), when slide (34) is advanced to the distal position.

Closure system (22) of surgical stapler (10) includes closure trigger (36) of handle assembly (12) and closure bar (50). As shown in FIGS. 2 and 4A-4C, closure trigger (36) is pivotably coupled with handle housing (30) about a pair of laterally extending posts (90). An upper arm (92) of closure trigger (36) having a vertically slotted distal portion is operatively coupled with a proximal end of closure bar (50) by a pair of closure links (96). A proximal end of each closure link (96) is pivotably coupled with a laterally extending post (93) of closure trigger upper arm (92). A distal end of each closure link (96) is pivotably coupled with the proximal end of closure bar (50) about a laterally extending post (54) of closure bar (50).

Figure 4A:
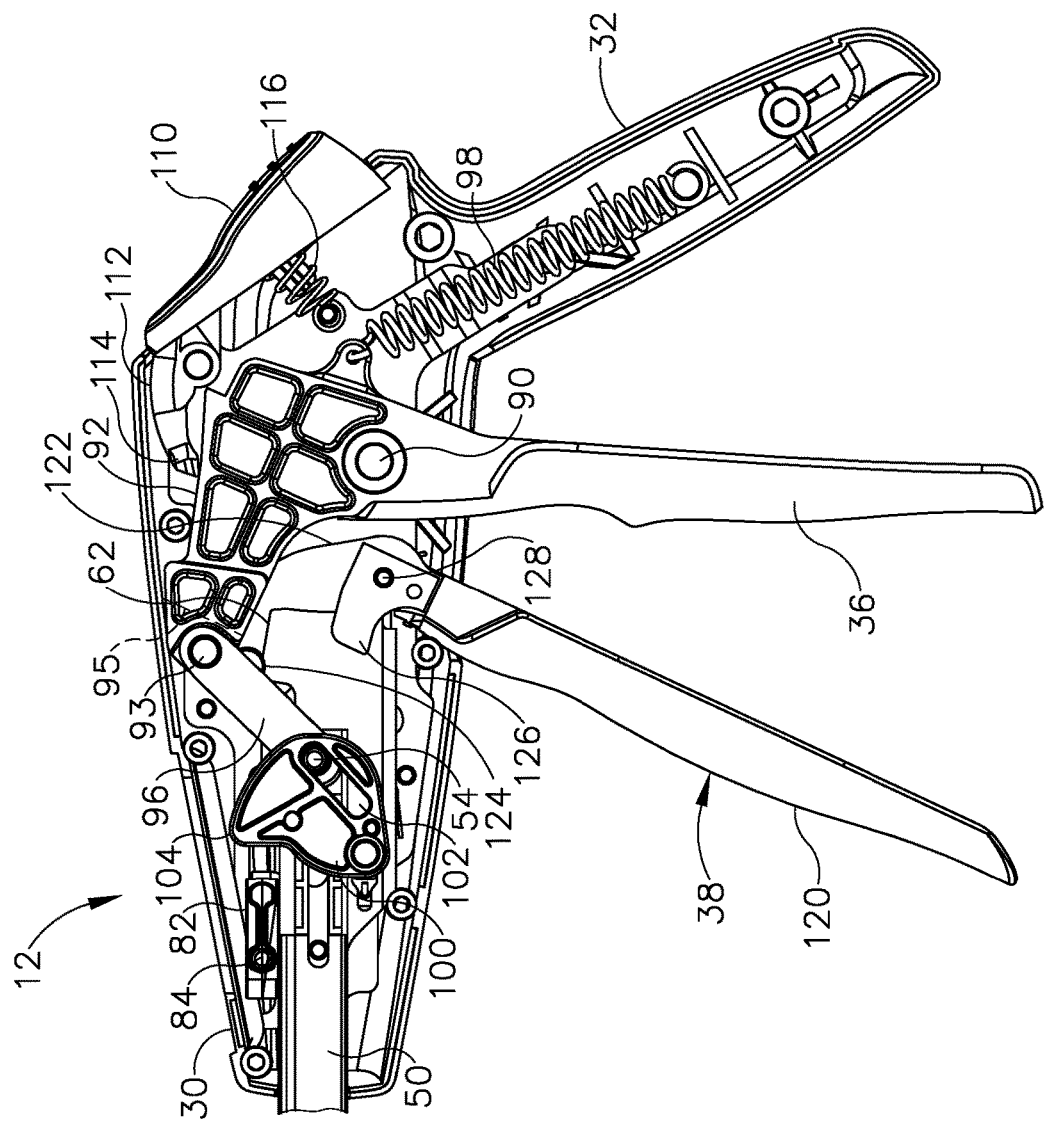
FIG. 4A depicts a side elevational view of the handle assembly of the surgical stapler of FIG. 1A, with various components omitted for clarity, showing the tissue retaining pin actuation system in an extended position to retain tissue while the closure system and the firing system are in unactuated states.
Figure 4B:
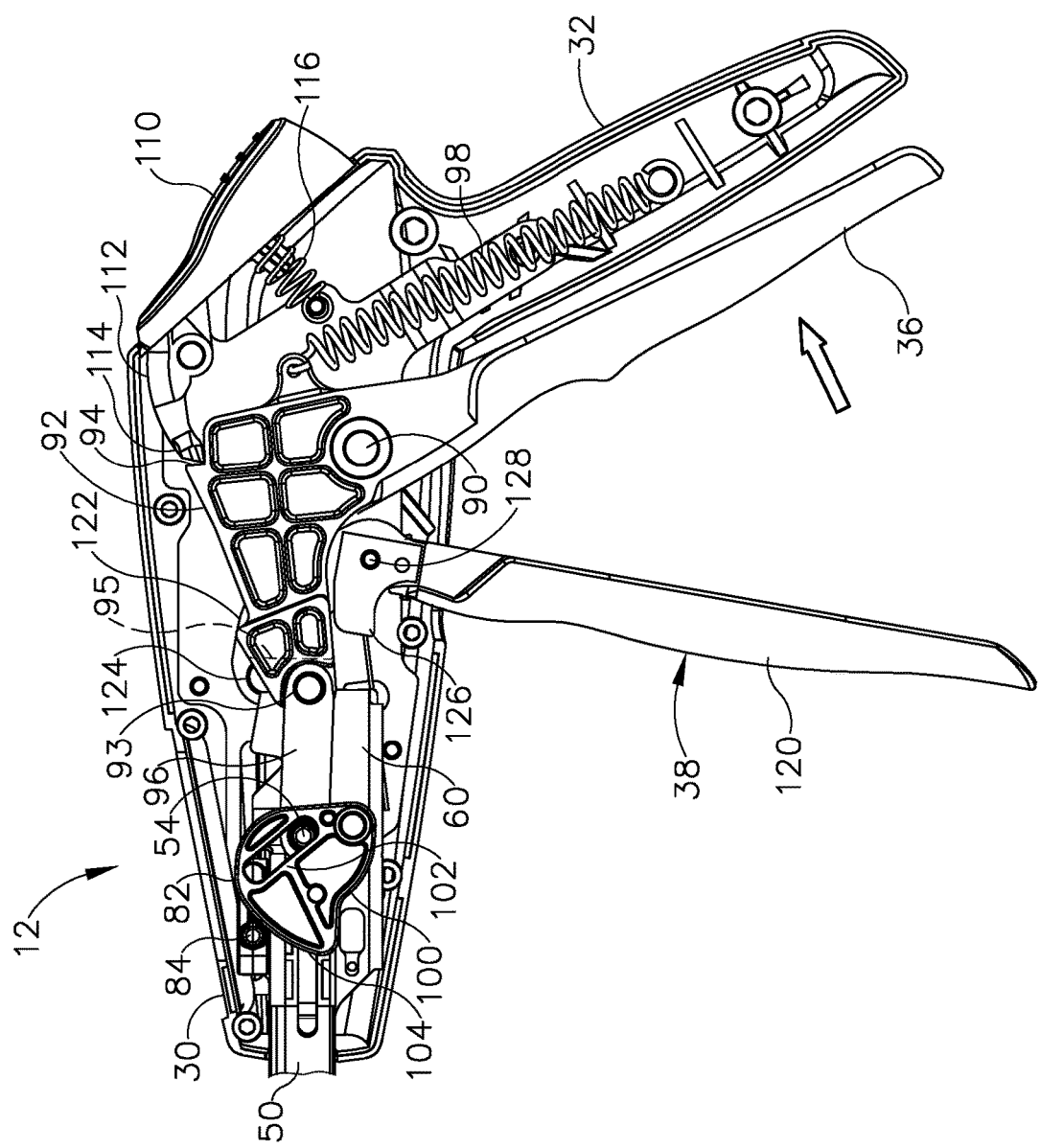
FIG. 4B depicts a side elevational view of the handle assembly of the surgical stapler of FIG. 1A, with various components omitted for clarity, showing the closure system actuated via a closure trigger to close the end effector and thereby clamp tissue.

As shown in FIGS. 4A-4B, pivoting of closure trigger (36) toward pistol grip (32) pivots advances closure trigger upper arm (92) distally and downwardly, thereby driving closure bar (50) distally via closure links (96). In turn, cartridge-receiving distal portion (52) of closure bar (50) drives cartridge housing (162) distally toward anvil (210). In this manner, end effector (16) is actuated from an open state (FIGS. 1A-1B) in which tissue is positionable within end effector (16), to a closed state (FIG. 1C) in which the tissue is clamped between cartridge housing (162) and anvil (210). A closure return spring (98) housed within pistol grip (32) of handle assembly (12) resiliently biases closure trigger (36) toward the unactuated state, and thus end effector (16) toward the open state.

In the present version, closure bar (50) is further configured to cooperate with tissue retaining pin actuation system (20) to automatically actuate retaining pin (176) distally to its extended position when an operator squeezes closure trigger (36). In that regard, as shown best in FIGS. 4A-4B, handle assembly (12) further includes a pair of camming yokes (100) rotatably disposed along the outer sides of closure links (96). Each camming yoke (100) includes an angled slot (102) that slidably receives a respective proximal post (54) of closure bar (50). As closure trigger (36) is actuated toward pistol grip (32), proximal posts (54) rotatably drive camming yokes (100) distally such that cam lobes (104) of yokes (100) engage corresponding side posts (84) of pushrod driver (82), thereby actuating pushrod (80) and thus tissue retaining pin (176) distally. Such automatic extension of tissue retaining pin (176) during closure of end effector (16) may be useful in the event that the operator does not manually actuate retaining pin (176) distally via slide (34) prior to actuating closure trigger (36).

Closure system (22) of the present example is further configured to releasably lock closure trigger (36) in the actuated position to provide effective clamping of tissue with end effector (16) without having to continuously squeeze closure trigger (36). As shown best in FIGS. 4A-4B, a release button (110) is pivotably disposed at a proximal end of handle assembly (12). A locking pawl (112) extends distally from an upper end of release button (110) and includes a pawl lug (114) that is resiliently biased into contact with an upper end of closure trigger upper arm (92), via a release button spring (116). Accordingly, pawl lug (114) is configured to slide along an upper surface of closure trigger upper arm (92) as closure trigger (36) is squeezed toward pistol grip (32). As shown in FIG. 4B, upon closure trigger (36) reaching a fully actuated position, pawl lug (114) drops into a proximal upper notch (94) of closure trigger upper arm (92), thereby locking closure trigger (36) in the fully actuated position. Should the operator wish to then reopen end effector (16), for example to reposition tissue within end effector (16) or otherwise release tissue once firing is complete, the operator may depress release button (110) to disengage pawl lug (114) from closure trigger (36). Via the resilient bias provided by closure return spring (98), closure trigger (36) then returns to the unactuated state and end effector (16) returns to the open state, shown in FIGS. 1A and 4A.

Firing system (24) of surgical stapler (10) includes firing trigger (38) of handle assembly (12), staple bar (60), knife bar (70), and staple driver member (186) and knife member (194) of staple cartridge unit (160). Features of knife bar (70) and staple driver member (186) are described in greater detail below in connection with FIG. 8. As shown in FIGS. 2 and 4A, firing trigger (38) of the present example is configured as an assembly having a lower shroud (120) that extends downwardly from handle housing (30) and is engageable by an operator; a pair of plates having arcuate upper arms (122) that extend upwardly and distally from lower shroud (120) and are positioned with handle housing (30); a rotatable cam pin (124) extending laterally between the free distal upper ends of arcuate upper arms (122); and a firing lockout projection (126) extending distally from the lower ends of arcuate upper arms (122) within handle housing (30). Cam pin (124) and other features of firing trigger (38) are described in greater detail below in connection with FIGS. 13-17.

Firing trigger (38) is pivotably coupled with handle housing (30) via a laterally extending pivot pin (128). Additionally, firing trigger (38) is positioned distal to closure trigger (36) such that arcuate upper arms (122) of firing trigger (38) are received into the slotted distal portion of closure trigger upper arm (92) as closure trigger (36) is actuated toward pistol grip (32). As shown in FIGS. 4A-4B, as the operator squeezes closure trigger (36) fully toward pistol grip (32), distally facing ledges (95) disposed within the distal slotted portion of closure trigger upper arm (92) engage cam pin (124) of firing trigger (38) and drive cam pin (124) distally by an initial amount. This causes the lower end of firing trigger (38) to pivot partially toward pistol grip (32) simultaneously with closure trigger (36), as shown in FIG. 4B.

Figure 4C:
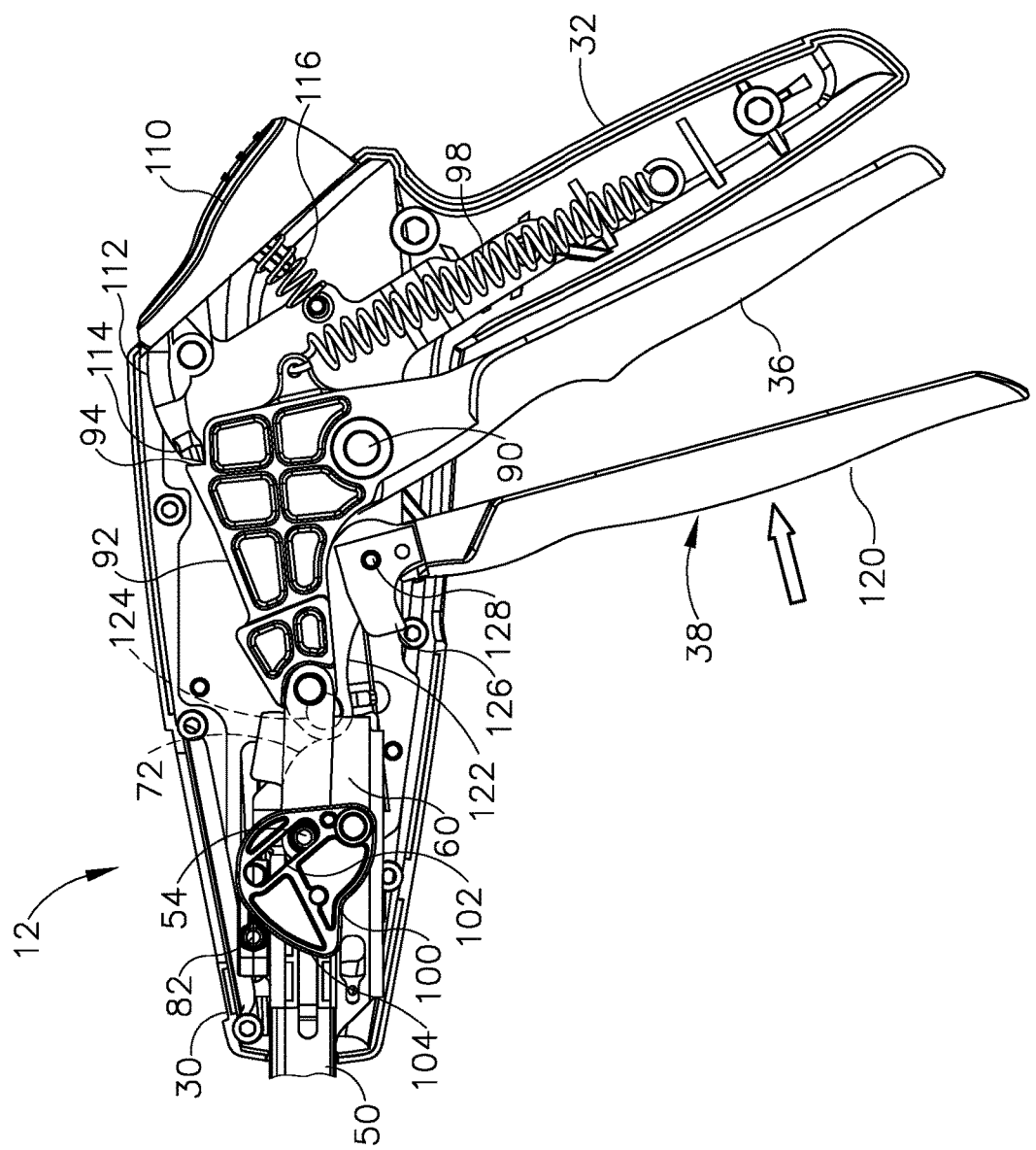
FIG. 4C depicts a side elevational view of the handle assembly of the surgical stapler of FIG. 1A, with various components omitted for clarity, showing the firing system actuated via a firing trigger to fire the end effector and thereby staple and cut tissue while the end effector remains in the closed state.
Figure 5:
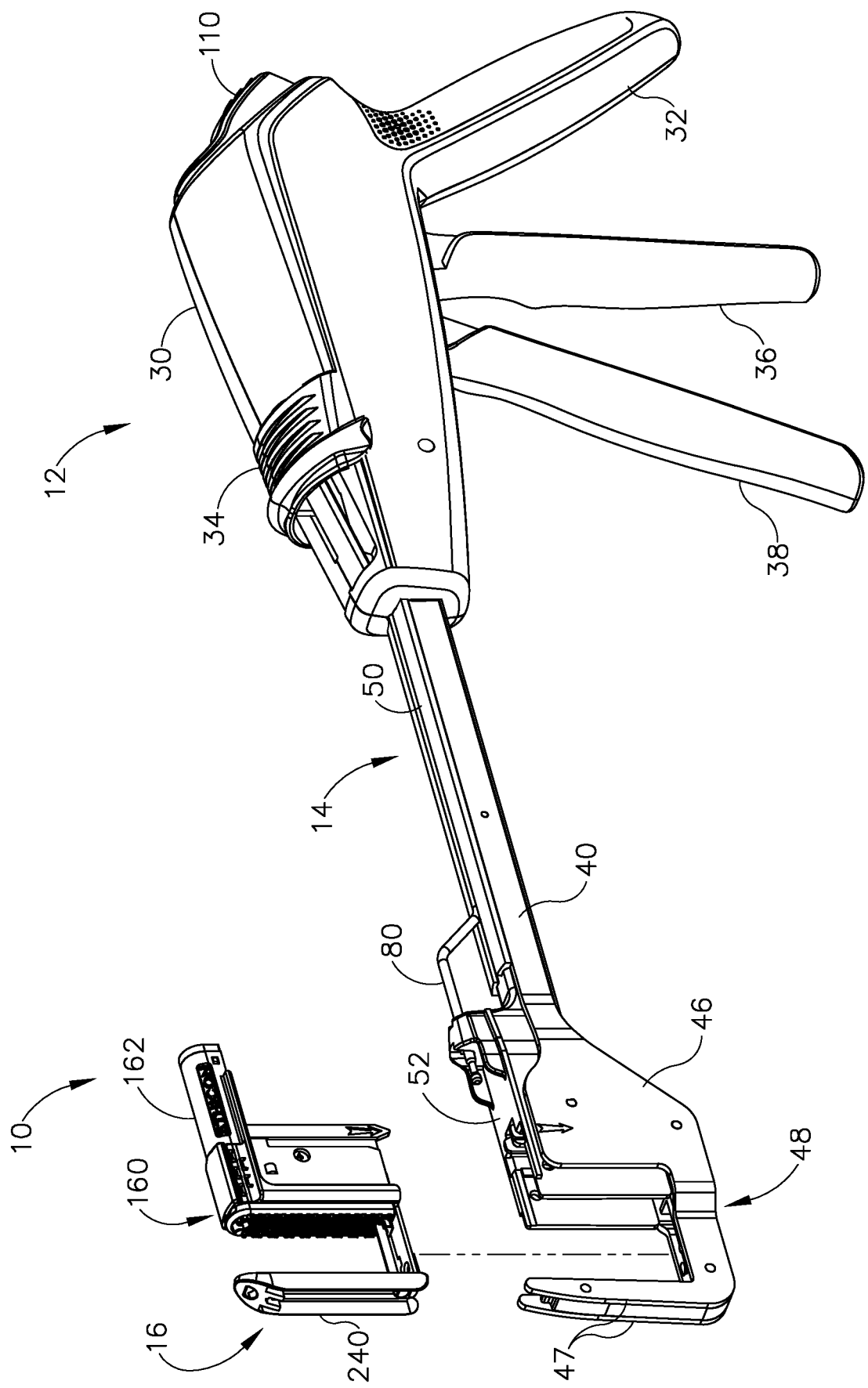
FIG. 5 depicts a perspective view of the surgical stapler of FIG. 1A, showing a staple cartridge unit of the end effector separated from a distal support structure of the end effector.

As shown in FIG. 4C, once end effector (16) has reached the fully closed state, further actuation of firing trigger (38) toward pistol grip (32) operates to "fire" end effector (16). In particular, outer portions of cam pin (124) engage proximal edges (62) of staple bar (60), thus driving staple bar (60) distally relative to closure bar (50). As described in greater detail below in connection with FIGS. 12A-12D, distal edges (64) of staple bar (60) engage a proximal end of staple driver member (186) within staple cartridge housing (162), thus driving staple driver member (186) distally through staple cartridge housing (162) to drive staples into tissue clamped by end effector (16). Actuation of firing trigger (38) toward its fully actuated state also causes a medial portion of cam pin (124), disposed between arcuate upper arms (122) of firing trigger (38), to engage a rounded proximal edge (72) of knife bar (70), thus driving knife bar (70) distally relative to closure bar (50). As described in greater detail below in connection with FIGS. 12A-12D, a distal edge (74) of knife bar (70) engages a proximal end of knife member (194) within staple cartridge housing (162), thus driving knife member (194) distally through staple driver member (186) to cut the tissue clamped by end effector (16).

Firing system (24) of the present example is suitably configured such that staple bar (60) and knife bar (70) translate distally together as firing trigger (38) is actuated through a primary range of motion toward pistol grip (32); and such that knife bar (70) continues to translate distally relative to staple bar (60) as firing trigger (38) is further actuated through a final range of motion toward pistol grip (32). Advantageously, such a configuration ensures that the tissue clamped by end effector (16) is fully stapled and that proper hemostasis is thus achieved along the intended tissue cut line before the tissue is cut by knife member (194).

As shown in FIG. 2, firing system (24) further includes a knife return spring (130) housed within handle assembly (12). Knife return spring (130) is anchored at its distal end to the distal end of knife bar (70), and at its proximal end to the distal end of closure bar (50). Accordingly, knife return spring (130) is operable to resiliently bias knife bar (70) proximally relative to closure bar (50) and staple bar (60) when firing trigger (38) is released. As shown in FIGS. 3 and 12A-12D, knife bar (70) includes a distal hook (76) that is captured by knife member (194) to thereby secure knife member (194) axially to knife bar (70). Accordingly, when the operator releases firing trigger (38) after completing a firing stroke, knife bar (70) and knife member (194) automatically retract proximally to safely house a distal cutting edge (200) of knife member (194) within staple cartridge housing (162).

As shown in FIG. 2, surgical stapler (10) of the present example further includes a proximal firing lockout mechanism in the form of a pivotable lever (140), which is operable to inhibit actuation of firing trigger (38) until end effector (16) has been fully closed by closure trigger (36). Firing lockout lever (140) is housed within handle assembly (12) and is pivotably mounted to an outer side of the proximal frame portion (42) of the left side plate (40). Firing lockout lever (140) is resiliently biased by a spring (146) toward a position in which a lower tab (142) of proximal lockout lever (140) blocks downward movement of firing lockout projection (126) of firing trigger (38), thus inhibiting actuation of firing trigger (38) when closure trigger (36) has not been fully actuated to close end effector (16). When closure trigger (36) reaches a fully actuated state, an upper arm (144) of firing lockout lever (140) is driven downwardly by pawl lug (114) of release button (110), thus rotating lower tab (142) away from firing lockout projection (126) and permitting actuation of firing trigger (38). Firing lockout lever (140) and other lockout features of surgical stapler (10) may be further configured and operable in accordance with at least some of the teachings of U.S. patent application Ser. No. 16/395,358, entitled "Clamping Based Lockout Mechanism for Right Angle Surgical Stapler," filed on Apr. 26, 2019, issued as U.S. Pat. No. 11,202,629 on Dec. 21, 2021, the disclosure of which is incorporated by reference herein.

Though not shown, shaft assembly (14) of surgical stapler (10) may include various additional components, such as an articulating joint, or may include a rearrangement of various components such that shaft assembly (14) may be modular relative to handle assembly (12).

B. End Effector of Surgical Stapler

End effector (16) of surgical stapler (10) includes distal support structure (48) defined by distal portions of side plates (40), cartridge-receiving distal portion (52) of closure bar (50), distal portions of staple bar (60) and knife bar (70), and replaceable staple cartridge unit (160). As shown best in FIGS. 5-8, staple cartridge unit (160) of the present version includes cartridge housing (162) and anvil (210) spaced apart from one another so as to define an axial gap (G) therebetween for receiving patient tissue to be stapled and cut. Cartridge housing (162) includes a distally facing deck (164) that is configured to clamp tissue against anvil (210) and extends transversely to a longitudinal axis of shaft assembly (14), along with anvil (210), thus providing end effector (16) with a "right angle" configuration.

Cartridge deck (164) includes an elongate linear knife slot (166) configured to slidably receive a knife (198) therethrough, and a plurality of staple openings (168) arranged in linear rows along either side of elongate linear knife slot (166) and configured to house a plurality of unformed staples (170) therein. Deck (164) of the present example further includes a plurality of stand-off features (172) interposed with staple openings (168) and configured to optimize grip and compression of patient tissue as the tissue is clamped between deck (164) and anvil (210). Deck (164) may be further configured in accordance with at least some of the teachings of U.S. patent application Ser. No. 16/234, 740, entitled "Surgical Stapler with Sloped Staple Deck for Varying Tissue Compression," filed Jan. 14, 2019, published as U.S. Pub. No. 2020/0205811 on Jul. 2, 2020, the disclosure of which is incorporated by reference herein.

An elongate upper body portion (174) of cartridge housing (162) slidably houses tissue retaining pin (176) and a couplet (180) secured to a proximal end of tissue retaining pin (176). Couplet (180) is configured to releasably couple tissue retaining pin (176) with a distal end of pushrod (80) of tissue retaining pin actuation system (20) when staple cartridge unit (160) is seated within distal support structure (48) of end effector (16). An end cap member (182) secured to a proximal end of upper body portion (174) is configured to constrain tissue retaining pin (176) and couplet (180) proximally within cartridge housing (162), while permitting tissue retaining pin (176) to translate between its proximal retracted position (see FIGS. 1A and 12A), and its distal extended position (see FIGS. 1B and 12B). Tissue retaining pin (176) includes a tapered distal tip (178) that is configured to pierce tissue as retaining pin (176) is extended toward anvil (210).

A lower body portion (184) of cartridge housing (162) slidably receives staple driver member (186) and knife member (194) therein. As shown best in FIG. 8, staple driver member (186) of the present version includes a base portion (188), a plurality of staple driver elements (190) projecting distally from base portion (188), and an interior channel (192) that extends axially through staple driver member (186) and is configured to slidably receive knife member (194). Each staple driver element (190) is configured to be slidably received within a respective staple opening (168) of cartridge housing (162) and drive a respective staple (170) from the opening (168) in response to actuation of closure trigger (36). While staple driver elements (190) of the present version are securely affixed to base portion (188), it will be appreciated that base portion (188) and staple driver elements (190) may be provided separately in other versions.

Knife member (194) includes a base portion (196) and a knife (198) secured to and extending distally from base portion (196) and having a distal cutting edge (200). Knife (198) is formed with a flat, plate-like shape that enables knife (198) to perform linear cuts on patient tissue. Knife member (194) is slidably received within interior channel (192) of staple driver member (186) such that knife (198) is configured to translate longitudinally through staple driver member (186) and elongate linear knife slot (166) of cartridge housing (162) for cutting tissue clamped by end effector (16) in response to full actuation of firing trigger (38).

As shown best in FIG. 8, anvil (210) of staple cartridge unit (160) includes a distal plate portion (212) and a coupling arm (214) extending proximally from a lower end of distal plate portion (212). Distal plate portion (212) is configured to cooperate with cartridge deck (164) to clamp tissue to be stapled and cut. Distal plate portion (212) includes an elongate linear slot (216) and a plurality of staple-forming pockets (218) arranged in linear rows along each side of slot (216). Pockets (218) are configured to receive and deform legs of staples (170) ejected from cartridge housing (162) for forming the staples (170) in tissue clamped between distal plate portion (212) and cartridge deck (164).

Figure 6:
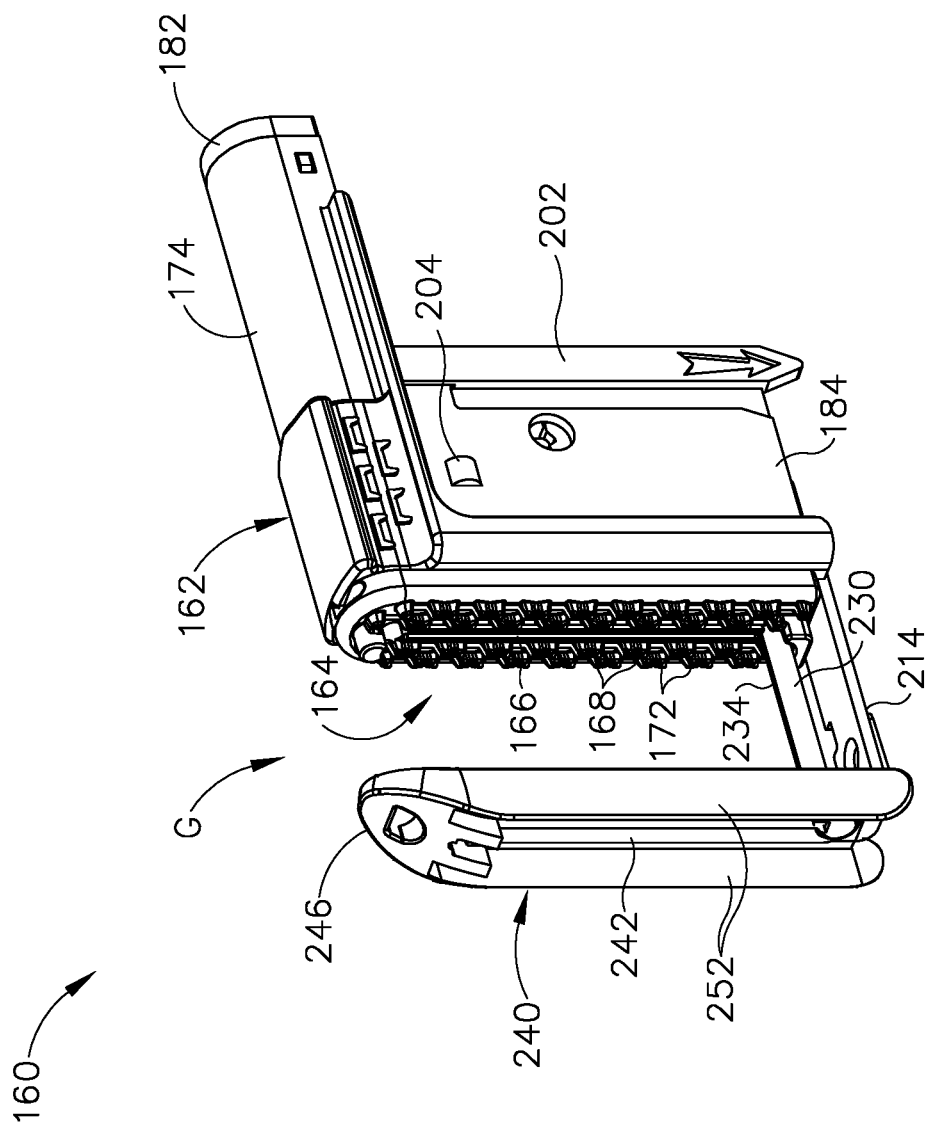
FIG. 6 depicts a distal left side perspective view of the staple cartridge unit of the surgical stapler of FIG. 1A.
Figure 7:
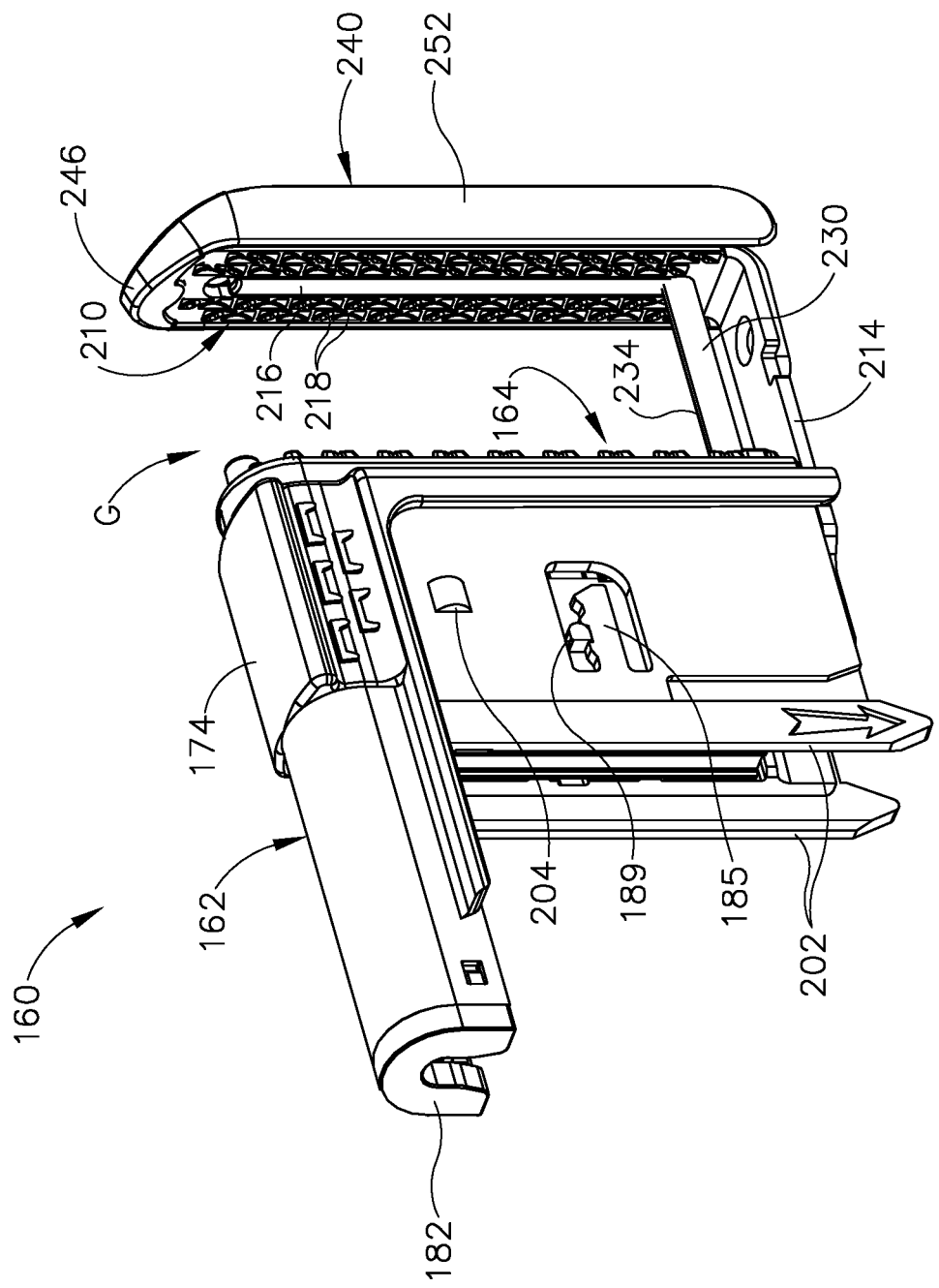
FIG. 7 depicts a proximal right side perspective view of the staple cartridge unit of the surgical stapler of FIG. 1A.
Figure 12A:
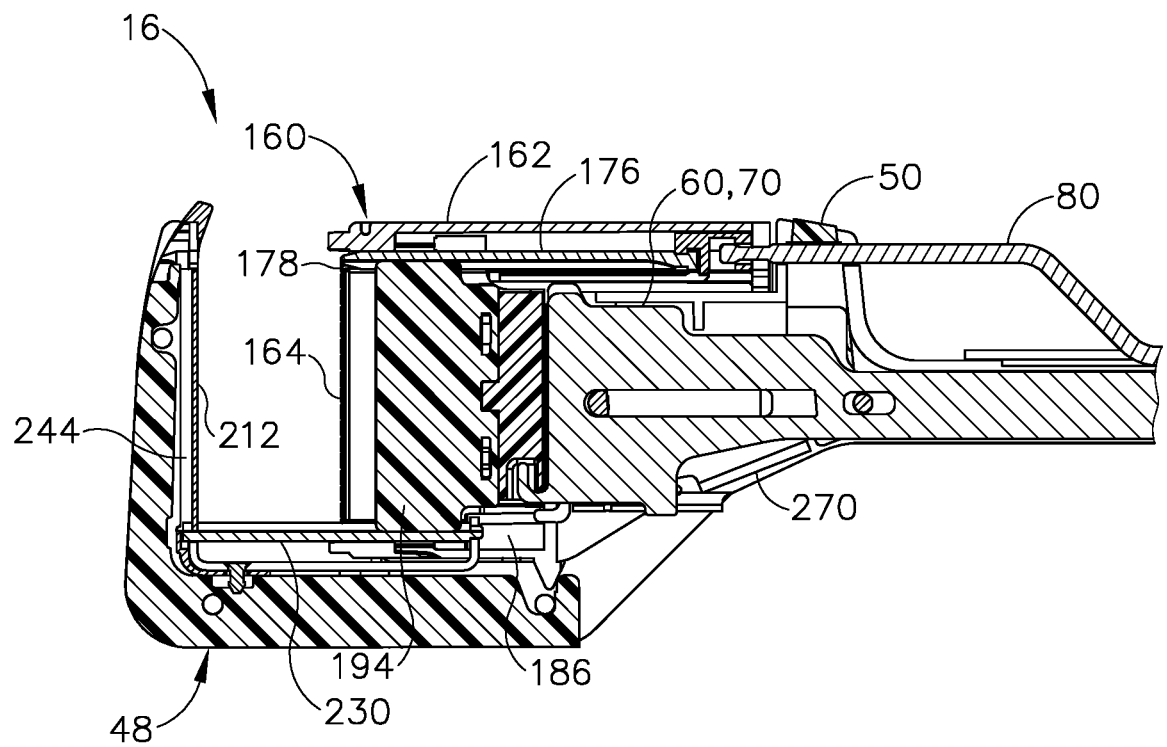
FIG. 12A depicts a side sectional view of the end effector of the surgical stapler of FIG. 1A, showing a tissue retaining pin in a retracted position while the end effector is in an open state.
Figure 12B:
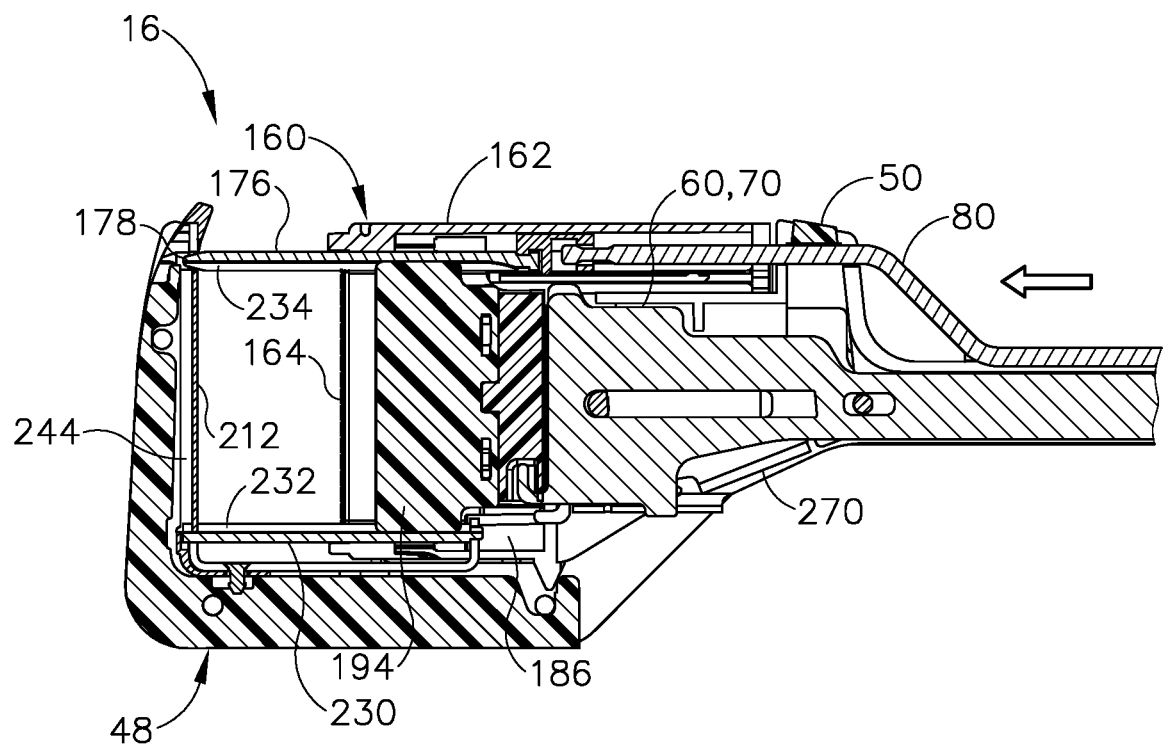
FIG. 12B depicts a side sectional view of the end effector of the surgical stapler of FIG. 1A, showing the tissue retaining pin in an extended position to retain tissue while the end effector remains in the open state.
Figure 12C:
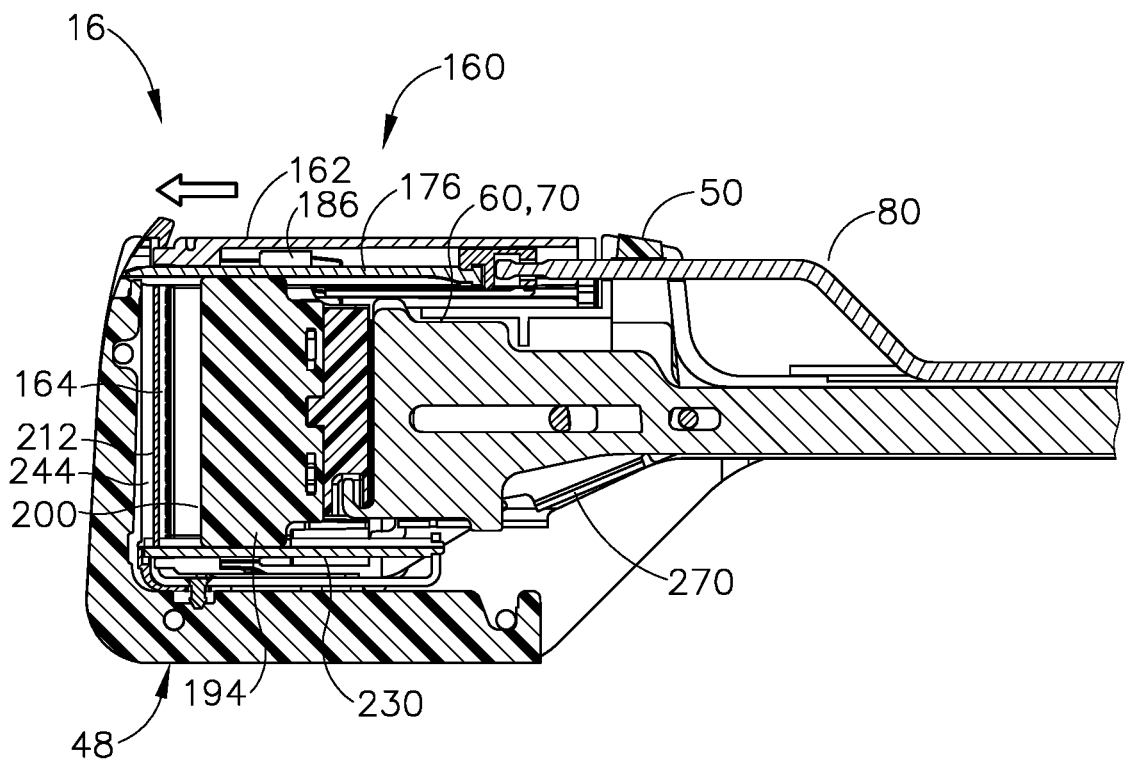
FIG. 12C depicts a side sectional view of the end effector of the surgical stapler of FIG. 1A, showing the end effector actuated to a closed state to clamp tissue while the tissue retaining pin remains in the extended position.

A guide pin (230) extends longitudinally between anvil plate portion (212) and cartridge housing (162) and is configured to guide longitudinal translation of cartridge housing (162) between the proximal open position (see FIGS. 1A and 12A) and the distal closed position (see FIGS. 1C and 12C). A proximal end of guide pin (230) is constrained by a proximal tab (220) of anvil coupling arm (214), shown in FIG. 8, and a distal end of guide pin (230) is constrained within a lower opening (222) formed in anvil plate portion (212). An upper opening (224) formed in anvil plate portion (212) is configured to receive and constrain tapered distal tip (178) of tissue retaining pin (176) in the extended position, such that tissue retaining pin (176) may cooperate with guide pin (230) to guide longitudinal translation of cartridge housing (162) relative to anvil (210). As seen in FIGS. 6-8, an inner side of guide pin (230) may include a longitudinal groove (232), which is configured to cooperate with a similar groove (234) (see FIGS. 12A-12D) to slidably guide knife (198) between retracted and extended positions relative to cartridge housing (162).

Staple cartridge unit (160) further includes a tissue cutting washer (240) fixed to anvil (210), and which is configured to cooperate with knife (198) to cut tissue clamped by end effector (16). As shown best in FIGS. 8 and 10-11, tissue cutting washer (240) includes an elongate, plate-like body (242) that extends along the distal side of anvil plate portion (212). Washer body (242) includes an elongate cutting element (244) that protrudes proximally through elongate slot (216) of anvil plate portion (212). Cutting element (244) functions as a cutting board by providing knife cutting edge (200) with a flat surface against which cutting edge (200) cuts tissue. At least cutting element (244) of tissue cutting washer (240) may comprise a polymeric material, such as high-density polyethylene (HDPE). In that regard, knife (198) may cut axially into cutting element (244), along its longitudinal centerline, when cutting tissue. While cutting element (244) of the present version provides a generally planar cutting surface, it will be appreciated that cutting element (244) may be alternatively configured in other versions.

Tissue cutting washer (240) further includes a rounded tip (246) at an upper end of washer body (242), and a coupling arm (248) extending proximally from a lower end of washer body (242). Washer tip (246) captures and thereby constrains an upper end of anvil plate portion (212), and its rounded configuration promotes atraumatic interaction with patient tissue. A press-fit pin (250) is configured to be inserted through openings formed in proximal coupling arms (214, 248) of anvil (210) and tissue cutting washer (240), thereby securely coupling anvil (210) and cutting washer (240) together.

Figure 10:
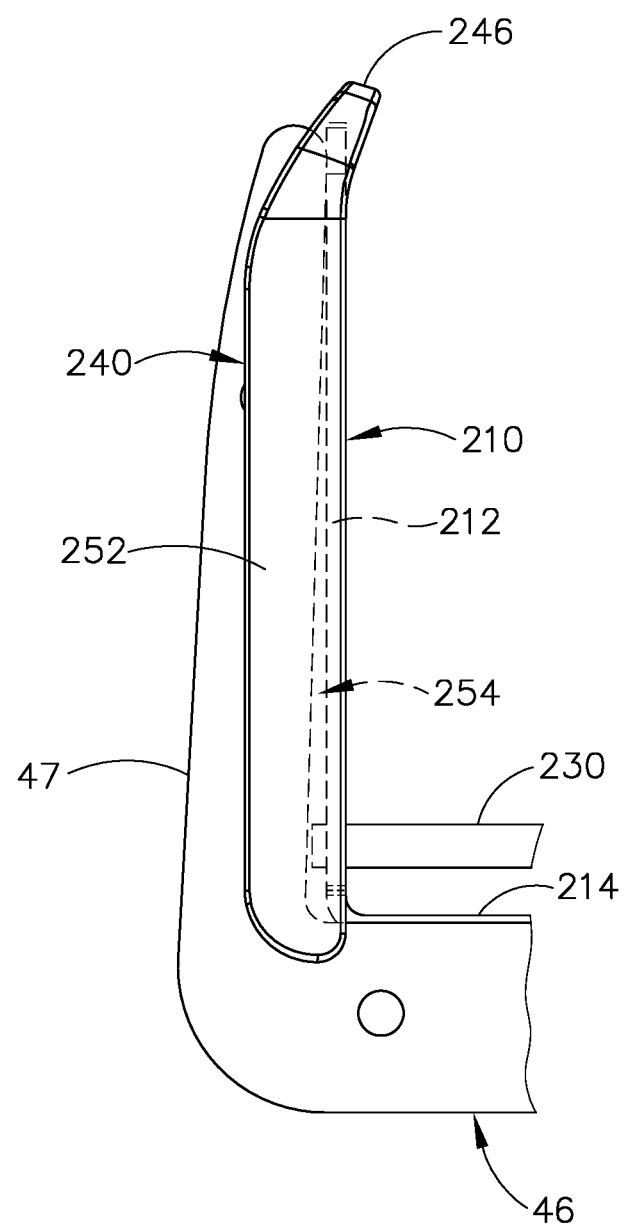
FIG. 10 depicts a side elevational view of a distal portion of the end effector of the surgical stapler of FIG. 1A following insertion of the staple cartridge unit into the distal support structure.
Figure 11:
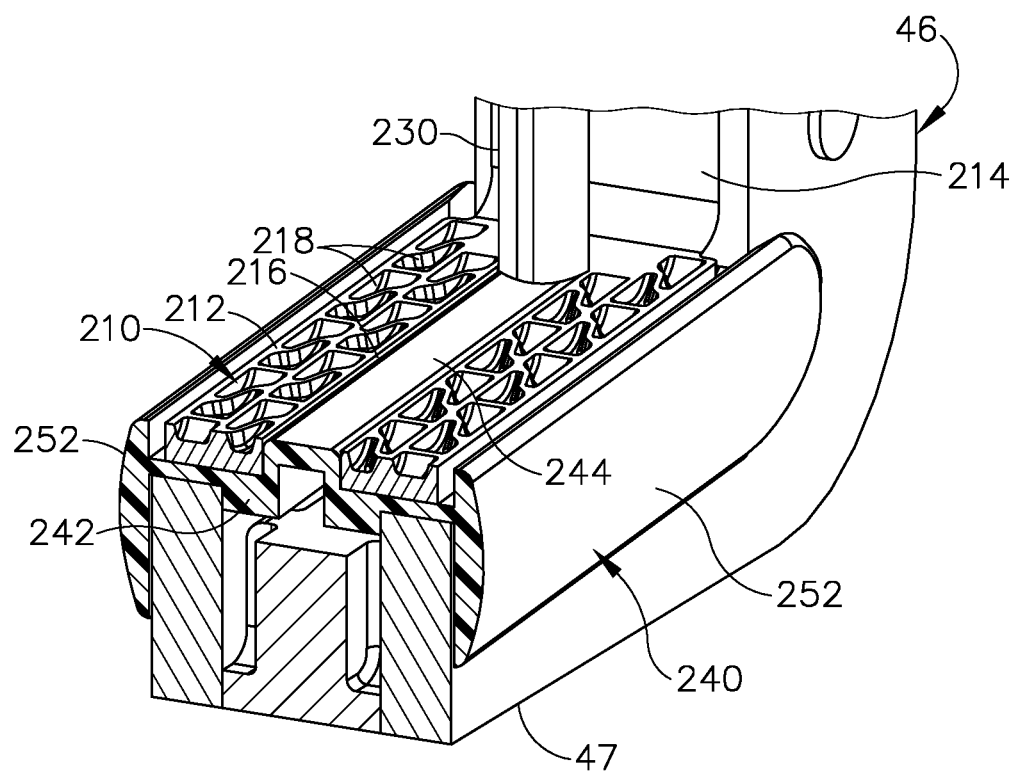
FIG. 11 depicts a sectional view of the distal portion of the end effector of the surgical stapler of FIG. 1A, showing interaction of a tissue cutting washer of the staple cartridge unit with the distal support structure.

Tissue cutting washer (240) further includes a pair of side flanges (252) that extend along a full length of anvil plate portion (212). As shown in FIGS. 10 and 11, each side flange (252) extends proximally to cover a respective side edge of anvil plate portion (212), and distally to cover at least a portion of distal hook (47) of the respective side plate (40) defining distal support structure (48). Accordingly, and advantageously, side flanges (252) function to cover an axial gap (254) that may form between anvil plate portion (212) and distal hooks (47), thereby preventing tissue from entering into and getting pinched within axial gap (254) in a manner that might otherwise result in undesirable trauma to the tissue. As shown in FIG. 11, the outer surfaces of side flanges (252) may be rounded to further enhance the atraumatic characteristics of the outer periphery of tissue cutting washer (240). Tissue cutting washer (240) may be further configured and operable in accordance with any of the teachings of U.S. patent application Ser. No. 16/395,357, entitled "Tissue Cutting Washer for Right Angle Surgical Stapler," filed on Apr. 26, 2019, issued as U.S. Pat. No. 11,266,403 on Mar. 8, 2022, the disclosure of which is incorporated by reference herein.

Figure 9B:
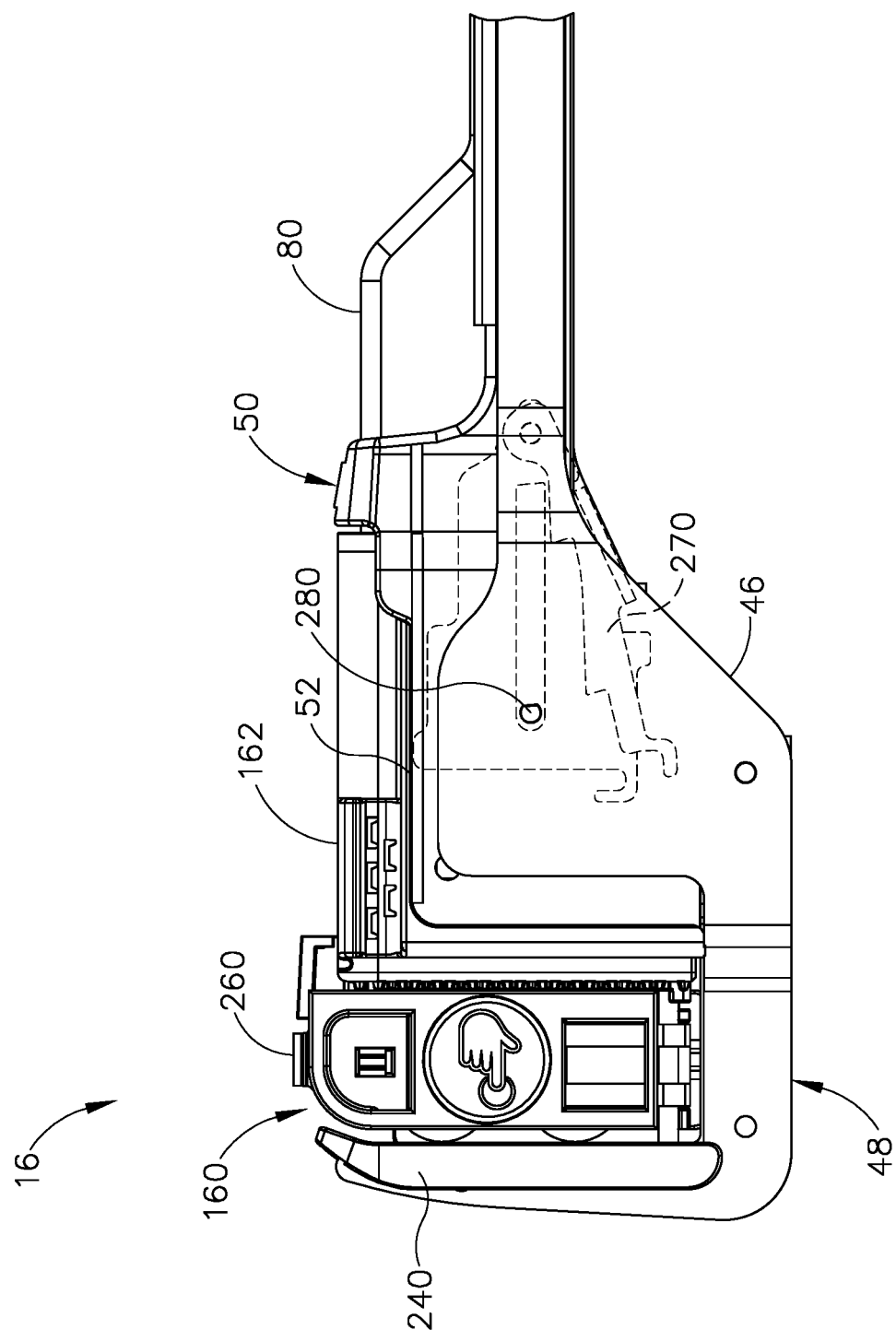
FIG. 9B depicts a side elevational view of the end effector of the surgical stapler of FIG. 1A, showing the lockout member in a bypass position when an unspent staple cartridge unit is seated within the distal support structure.

C. Exemplary Loading of Staple Cartridge Unit into Distal Support Structure of End Effector FIGS. 9A and 9B show loading of staple cartridge unit (160) in its unused (or "unspent") state into distal support structure (48) of end effector (16). As shown in FIG. 9A, and as described briefly above, distal support structure (48) is configured with a U-shaped side profile having a distal side defined by distal hooks (47), a proximal side defined by a proximal portion of distal jaw portion (46) and a distal end of cartridge-receiving distal portion (52) of closure bar (50), and an upwardly opening axial gap disposed therebetween.

Staple cartridge unit (160) is shown in FIGS. 9A-9B provided with a staple retainer (260) that is removably positioned between deck (164) and anvil plate portion (212) to retain staples (170) within staple openings (168), and to ensure proper axial spacing between deck (164) and anvil plate portion (212) as staple cartridge unit (160) is inserted into distal support structure (48). Upon removal of staple retainer (260), staple cartridge unit (160) presents a U-shaped side profile similar to that of distal support structure (48), with a distal side defined by anvil plate portion (212) and tissue cutting washer (240), a proximal side defined by cartridge deck (164), and upwardly opening axial gap (G) disposed therebetween. Staple retainer (260) may be configured and operable in accordance with any of the teachings of U.S. patent application Ser. No. 16/395,364, entitled "Staple Retainer for Right Angle Surgical Stapler," filed on Apr. 26, 2019, issued as U.S. Pat. No. 11,166,721 on Nov. 9, 2021, the disclosure of which is incorporated by reference herein.

As shown in FIG. 9A, the user first aligns proximal side rails (202) formed on lower body portion (184) of cartridge housing (162) with inner channels (56) formed in cartridge-receiving distal portion (52) of closure bar (50) (see FIG. 3). As shown in FIG. 9B, the user then presses staple cartridge unit (160) downwardly into distal support structure (48) of end effector (16) such that proximal side rails (202) of cartridge housing (162) slide downwardly into inner channels (56) of closure bar (50), and such that distal hooks (47) of side plates (40) slide into grooves formed in the distal side of tissue cutting washer body (242) (see FIG. 11). As staple cartridge unit (160) fully seats within distal support structure (48), detent protrusions (204) formed on lower body portion (184) of cartridge housing (162) are receiving within respective openings (58) formed in cartridge-receiving distal portion (52) of closure bar (50), thereby removably securing staple cartridge unit (160) within distal support structure (48). Engagement of cartridge detent protrusions (204) with openings (58) may provide the user with tactile and/or audible feedback to confirm that staple cartridge unit (160) has been fully seated within distal support structure (48).

As shown in FIG. 9A, a distal lockout lever (270) is pivotably coupled to a distal end of staple bar (60). Distal lockout lever (270) extends distally toward distal edges (64) of staple bar (60) and knife bar (70) and is configured to releasably engage a fixed distal pin (280) that extends laterally through distal portions of side plates (40), closure bar (50), staple bar (60), and knife bar (70). Distal lockout lever (270) is resiliently biased toward a raised position shown in FIG. 9A and is pivotable toward a lowered position shown in FIG. 9B in response to engagement by a proximal end of staple driver member (186) upon insertion of an unspent staple cartridge unit (160) into distal support structure (48). In the raised position, distal lockout lever (270) lockingly engages fixed distal pin (280) and thereby inhibits distal actuation of staple bar (60) and knife bar (70), and thus firing of staple cartridge unit (160). In the lowered position, distal lockout lever (270) disengages fixed distal pin (280) and thus permits distal actuation of staple bar (60) and knife bar (70) for firing of staple cartridge unit (160). Distal lockout lever (270) is described in greater detail below in connection with FIGS. 18-22E.

D. Exemplary Actuation of Surgical Stapler

Having described various structural features of surgical stapler (10) above, including staple cartridge unit (160), exemplary actuation of surgical stapler (10) during a surgical procedure will now be described below. After loading an unspent staple cartridge unit (160) into distal support structure (48) in the manner described above, end effector (16) is then suitably manipulated within a body cavity of a patient to position patient tissue within staple cartridge gap (G), between anvil plate portion (212) and cartridge deck (164). As shown in FIGS. 12A and 12B, pushrod (80) is then actuated distally via slide (34) to drive pushrod (80) distally, thereby extending tissue retaining pin (176) from cartridge housing (162) so that its distal tip (178) pierces through any tissue overlying the upper end of cartridge deck (164) and seats within the upper end of anvil plate portion (212). In this manner, the patient tissue is securely retained within cartridge gap (G) before closure.

As shown in FIG. 12C, closure bar (50) is then actuated distally via closure trigger (36), thereby driving cartridge housing (162) distally along guide pin (230) and tissue retaining pin (176) to clamp tissue between cartridge deck (164) and anvil plate portion (212). As shown in the present example, staple bar (60) and knife bar (70) actuate distally with closure bar (50) and cartridge housing (162) so that staple driver member (186) and knife member (194) are suitably positioned for firing upon full closure of end effector (16). As described above, end effector (16) is releasably maintained in the fully closed state by locking pawl (112) of release button (110) of handle assembly (12).

Figure 12D:
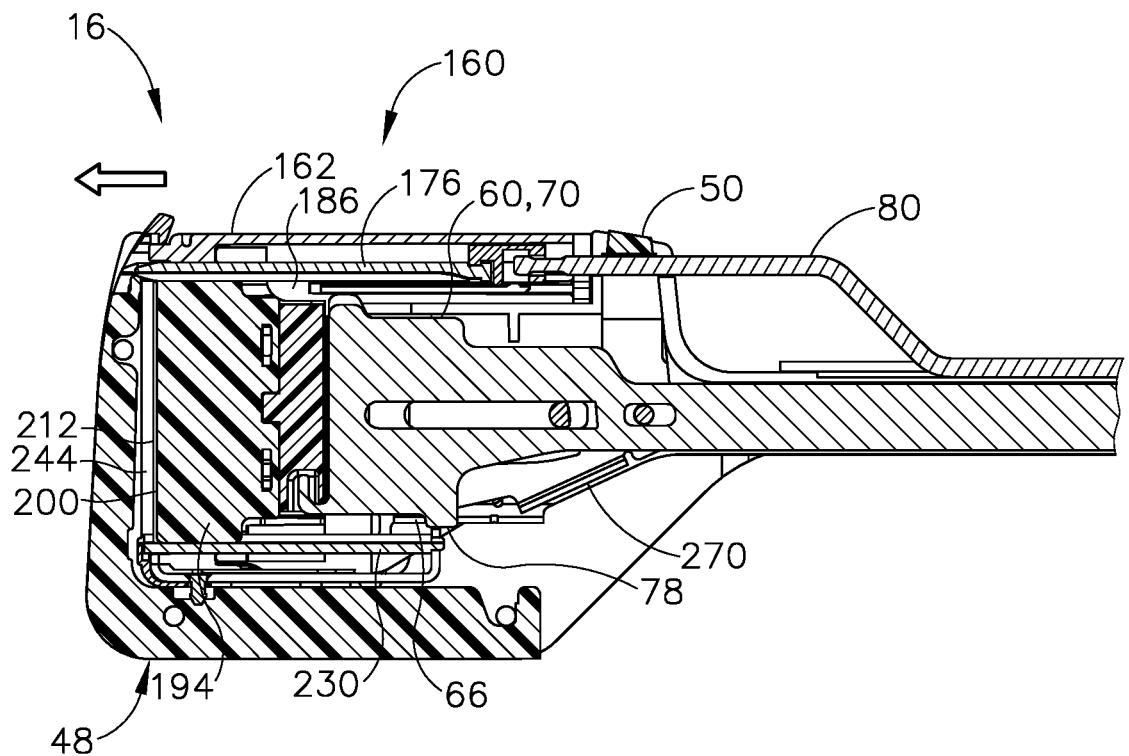
FIG. 12D depicts a side sectional view of the end effector of the surgical stapler of FIG. 1A, showing the end effector further actuated to a fired state to staple and cut tissue while remaining in the closed state.

As shown in FIG. 12D, staple bar (60) and knife bar (70) are then actuated distally via firing trigger (38), thereby driving staple driver member (186) and knife bar (70) distally through cartridge housing (162). Staple driver elements (190) of staple driver member (186) advance distally through staple openings (168), thereby driving staples (170) housed therein distally through the clamped tissue and into staple-forming pockets (218) of anvil plate portion (212), such that the staples (170) are formed in the tissue. Knife member (194) drives knife (198) distally through elongate knife slot (166) of cartridge deck (164), through the clamped tissue, and against cutting element (244) of tissue cutting washer (240), thereby severing the clamped tissue along a linear cut line between the innermost rows of formed staples (170). Upon cutting fully through the clamped tissue, knife cutting edge (200) may penetrate distally into cutting element (244) of tissue cutting washer (240). Optionally, in response to such penetration, tissue cutting washer body (242) may fracture along knife cutting edge (200), thereby providing an audible indication (e.g., via a "snapping" sound) to the surgeon that the firing stroke is complete and that the clamped tissue has been fully stapled and severed.

As described above, and as shown in FIG. 12D, staple driver member (186) and knife member (194) may translate distally together through staple cartridge housing (162) as firing trigger (38) is actuated through a primary range of motion that results in stapling of the tissue. As shown in FIG. 12D, knife member (194) may then continue translating distally relative to a stationary staple driver member (186) as firing trigger (38) is further actuated through a final range of motion that results in cutting of the stapled tissue with knife (198). In this manner, the tissue clamped by end effector (16) is fully stapled before being severed.

As shown best in FIG. 7, a first lateral side of lower body portion (184) of cartridge housing (162) includes a detent arm (185) having a plurality of axially spaced recesses. Additionally, a first lateral side of base portion (188) of staple driver member (186) includes a laterally extending detent post (189), which is configured to detent axially along detent arm (206) as staple driver member (186) is driven distally through cartridge housing (162) when stapling clamped tissue. As shown best in FIG. 8, a second lateral side of base portion (188) of staple driver member (186) includes a detent arm (191) having a plurality of axially spaced recesses. Additionally, a second lateral side of base portion (196) of knife member (194) includes a laterally extending detent post (197), which is configured to detent axially along detent arm (191) as knife member (194) is driven distally through staple driver member (186) when cutting clamped tissue. Such detent features may provide the surgeon with tactile feedback when staple driver member (186) has been fully extended to staple the tissue, and subsequently when knife member (194) has been fully extended to cut the stapled tissue.

Once surgical stapler (10) has been fully fired, the surgeon releases firing trigger (38), which enables knife bar (70) and knife member (194) to automatically retract proximally relative to closure bar (50) via the resilient bias of knife return spring (130), described above. In the present version, knife bar (70) is operatively coupled with staple bar (60) such that proximal retraction of knife bar (70) relative to closure bar (50) also drives proximal retraction of staple bar (60) relative to closure bar (50); for example, via engagement of a lower tab (78) formed on a distal portion of knife bar (70) with a lower slot (66) formed in the underside of a distal portion of staple bar (60). Meanwhile, stapling detent features (185, 189) described above operate to maintain staple driver member (186) in its fully extended position within cartridge housing (162), such that distal lockout lever (270) disengages staple driver member (186). This allows distal lockout lever (270) to return to a raised lockout position and block re-actuation of firing trigger (38) now that staple cartridge unit (160) is spent. In this manner, distal lockout lever (270) prevents a surgeon from inadvertently re-firing spent staple cartridge unit (160) into tissue in a manner that would sever the tissue with knife (198) without applying staples.

Following release of firing trigger (38), the surgeon then depresses release button (110) on handle assembly (12) to permit closure trigger (36) and closure bar (50) to return to their unactuated states via the resilient bias of closure return spring (98), described above. Such proximal retraction of closure bar (50) draws cartridge housing (162) proximally away from anvil (210) so that the stapled and cut tissue may be released from end effector (16). Proximal retraction of closure bar (50) also draws staple bar (60) and knife bar (70) further proximally to their proximal home positions so that spent staple cartridge unit (160) may be removed from distal support structure (48) and replaced with a new staple cartridge unit (160).

E. Additional Features of Firing System

Figure 13:
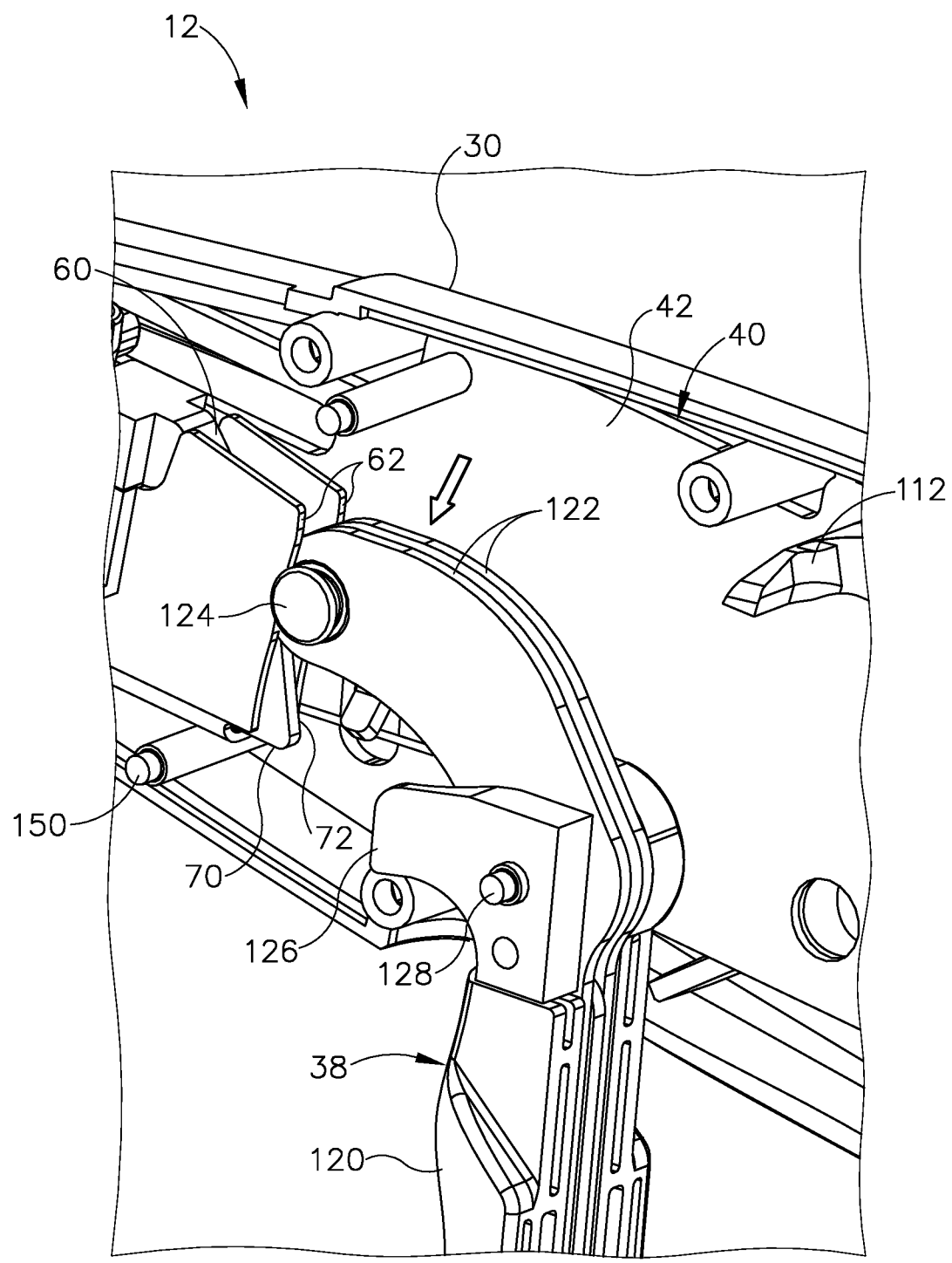
FIG. 13 depicts an enlarged perspective view of the handle assembly of the surgical stapler of FIG. 1A, with various components omitted for clarity, showing actuation of the firing system via pivoting of the firing trigger.
Figure 14:
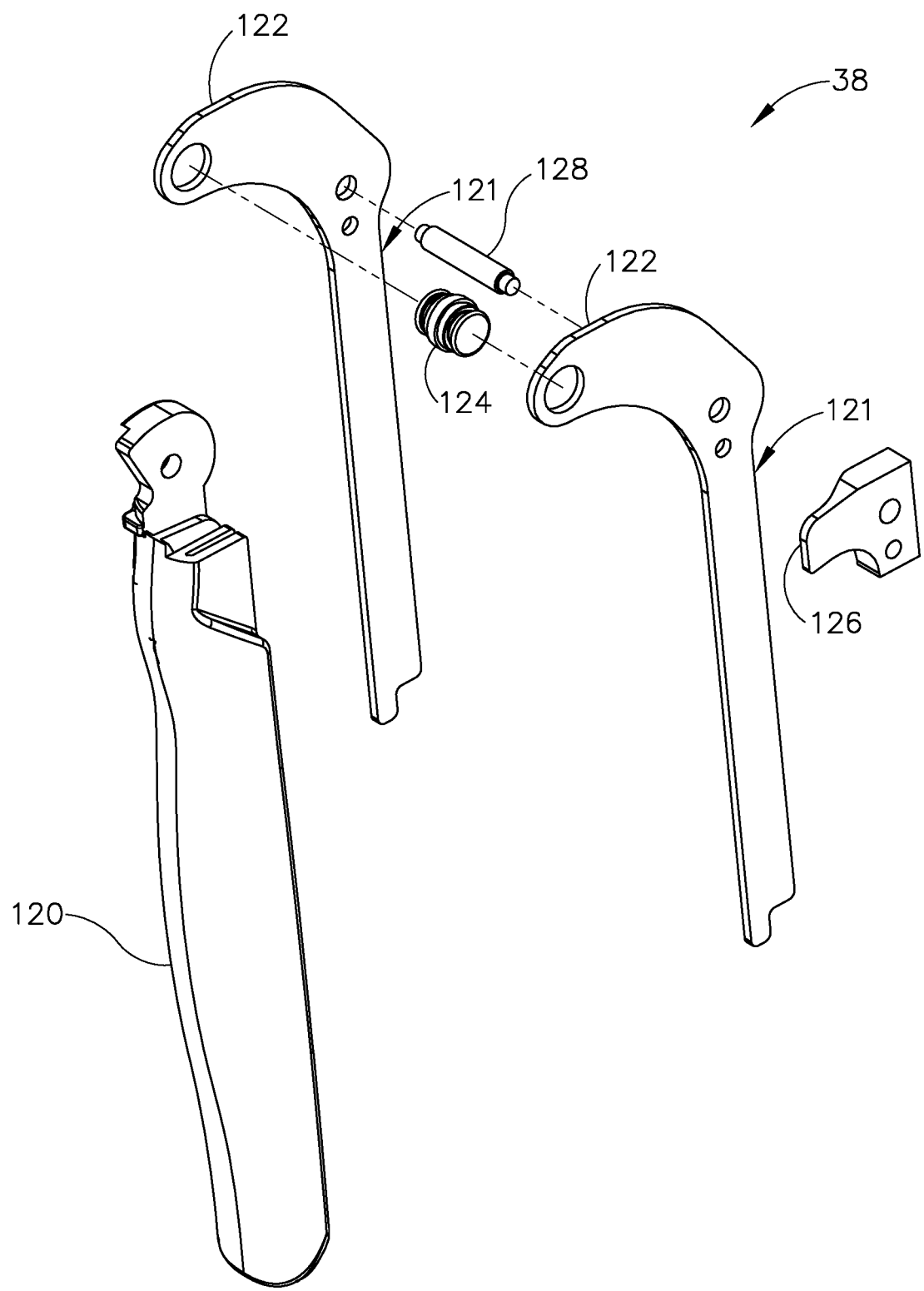
FIG. 14 depicts a disassembled perspective view of the firing trigger of the surgical stapler of FIG. 1A.

FIGS. 13-17 show additional features of firing trigger (38) and its engagement with staple bar (60) and knife bar (70) during a firing stroke for firing end effector (16). As shown in FIGS. 13-14 and as described briefly above, firing trigger (38) is configured as an assembly that includes trigger shroud (120); a pair of trigger side plates (121) nested within trigger shroud (120) and each having an arcuate upper arm (122); cam pin (124) spanning laterally between and rotatably supported by the distal ends of arcuate upper arms (122); firing lockout element (126) disposed on the lateral side of the left trigger side plate (121); and trigger pivot pin (128), which extends laterally through trigger shroud (120), trigger side plates (121), and firing lockout element (126), to pivotably couple firing trigger (38) with handle assembly body (30).

Figure 15:
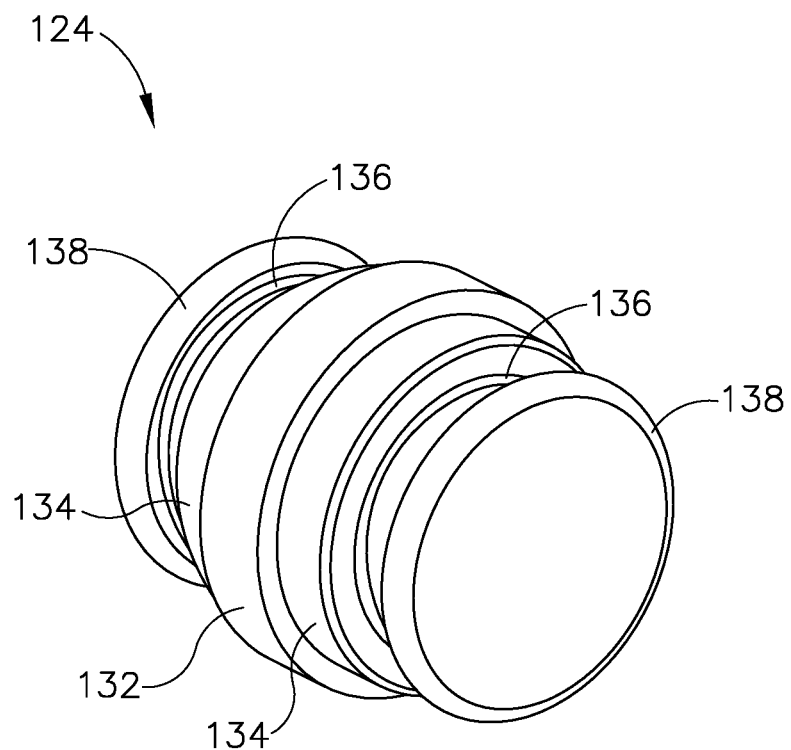
FIG. 15 depicts a perspective view of a rotatable cam pin of the firing trigger of the surgical stapler of FIG. 1A.

As shown best in FIG. 15, rotatable cam pin (124) of firing trigger (38) includes features that define a plurality of stepped diameters spaced laterally along a central rotational axis of cam pin (124). These features of cam pin (124) include a circular central body (132); a circular recessed shoulder (134) disposed on each lateral side of central body (132); an annular groove (136) disposed at the laterally outward side of each recessed shoulder (134); and an endcap (138) disposed at the laterally outward side of each annular groove (136). As described below, these features enable cam pin (124) to engage the proximal ends of staple bar (60) and knife bar (70) simultaneously in response to squeezing of firing trigger (38) toward pistol grip (32) for firing end effector (16).

Figure 16:
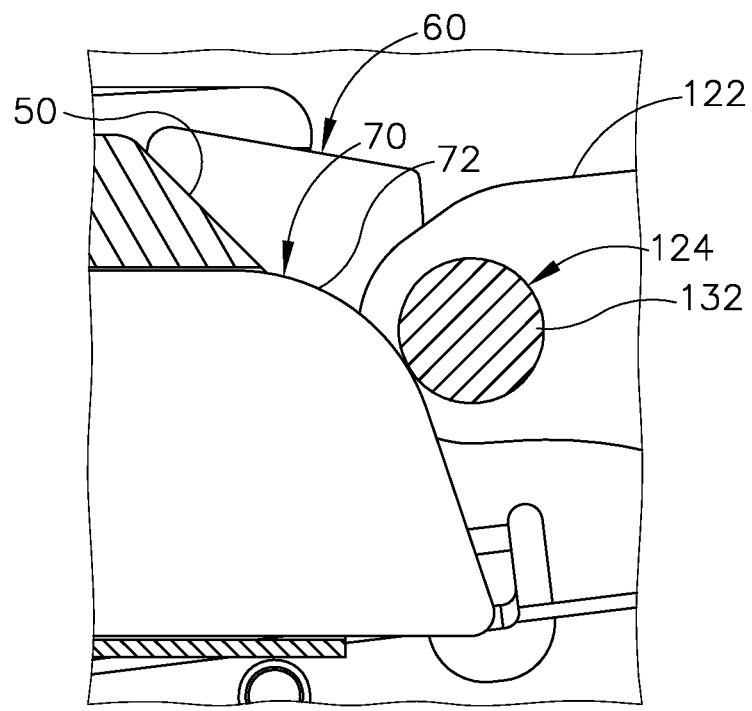
FIG. 16 depicts a side sectional view of a proximal end of the firing system of the surgical stapler of FIG. 1A, showing engagement of an outer portion of the cam pin with a proximal edge of the staple bar of the firing system.
Figure 17:
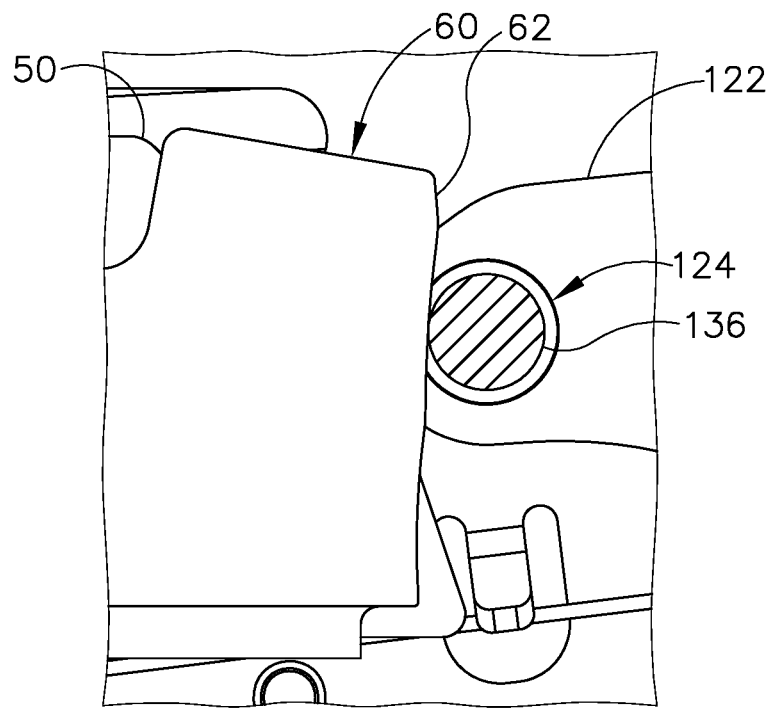
FIG. 17 depicts another side sectional view of a proximal end of the firing system of the surgical stapler of FIG. 1A, showing engagement of an inner portion of the cam pin with a proximal edge of the knife bar of the firing system.

As shown in FIG. 16, circular central body (132) of cam pin (124) is configured to engage rounded proximal edge (72) of knife bar (70) in response to squeezing of firing trigger (38). Simultaneously, each annular groove (136) of cam pin (124) is configured to engage a respective proximal edge (62) of staple bar (60) in response to squeezing of firing trigger (38). Accordingly, squeezing of firing trigger (38) toward pistol grip (32) to perform a firing stroke causes cam pin (124) to drive staple bar (60) and knife bar (70) distally, thereby firing end effector (16) in the manner described above. Because cam pin (124) is rotatably mounted to trigger side plates (121), cam pin (124) is configured to roll along proximal edges (62) of staple bar (60) and knife bar (70) as firing trigger (38) is squeezed. Advantageously, such rolling minimizes frictional forces between cam pin (124) and proximal edges (62), and thus minimizes an input force that an operator must exert on firing trigger (38) to fully actuate bars (60, 70) distally to fire end effector (16) (also referred to as "force to fire").

Forces exerted by cam pin (124) on staple bar (60) and knife bar (70) during a firing stroke may result in the proximal portions of bars (60, 70) experiencing a downward bending moment about their proximal-most support point within shaft assembly (14). As seen best in FIG. 13, a support pin (150) is positioned beneath the proximal ends of staple bar (60) and knife bar (70). Support pin (150) is configured to support bars (60, 70) at their undersides to counteract such a bending moment and prevent downward deflection of bars (60, 70) during firing. In the present example, support pin (150) spans laterally between proximal frame portions (42) of stapler side plates (40) and is fixed in a longitudinal direction of stapler side plates (40), and in some versions support pin (150) may be rotatable relative to side plates (40).

F. Distal Lockout Mechanism of Surgical Stapler

Figure 18:
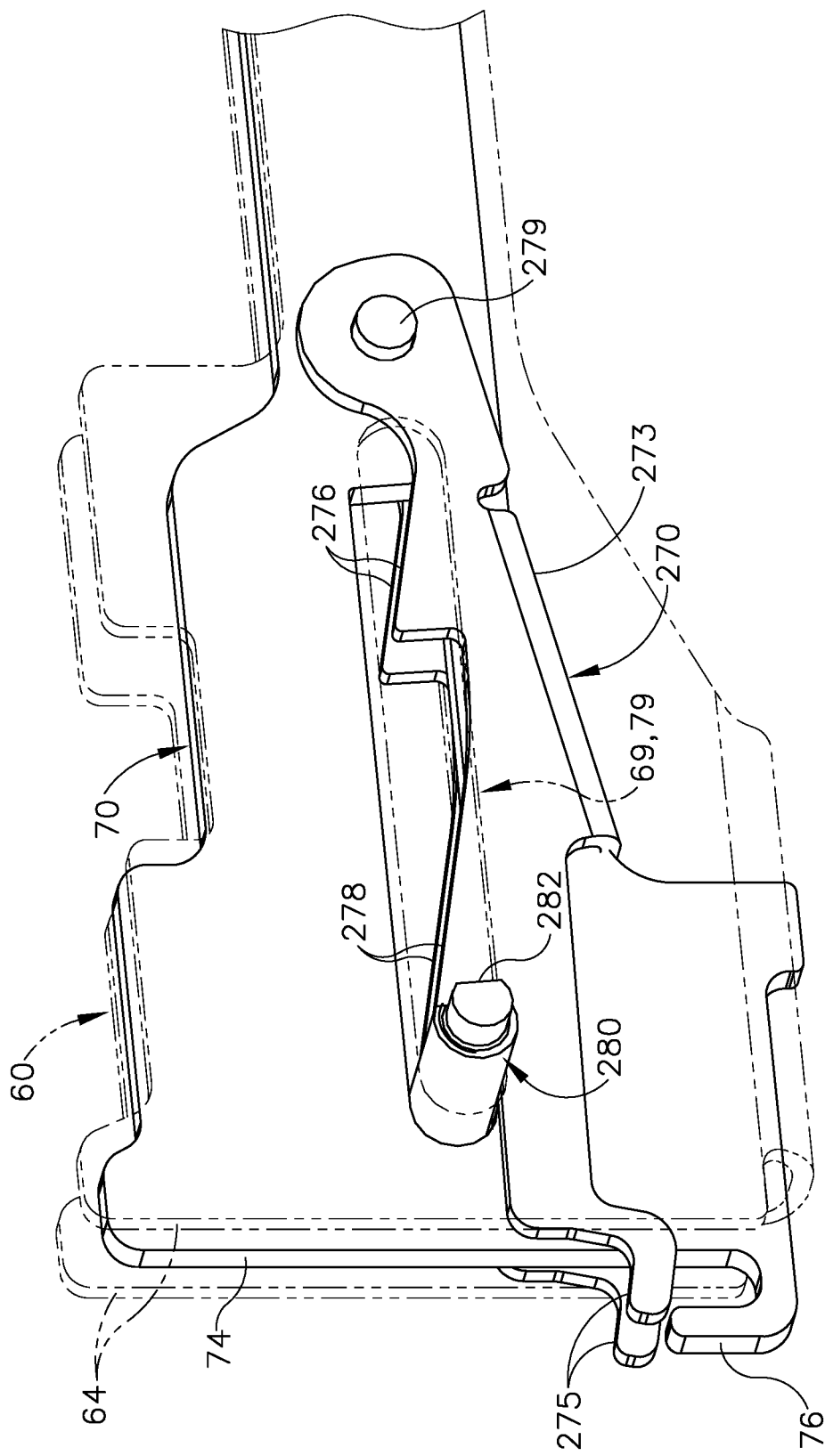
FIG. 18 depicts a perspective view of a distal portion of the firing system of the surgical stapler of FIG. 1A, with various components omitted for clarity, showing an exemplary distal lockout mechanism operable to inhibit actuation of the closure system and the firing system.

As shown in FIG. 18, surgical stapler includes a distal lockout mechanism that includes a dual lockout member in the form of lockout lever (270), and a stop member in the form of fixed pin (280). As described briefly above and in greater detail below, distal lockout lever (270) and fixed pin (280) are configured to cooperate to inhibit closure of end effector (16) when an unspent staple cartridge (160) is absent from end effector (16), and to inhibit firing of end effector (16) more than once with the same staple cartridge unit (160).

Figure 19:
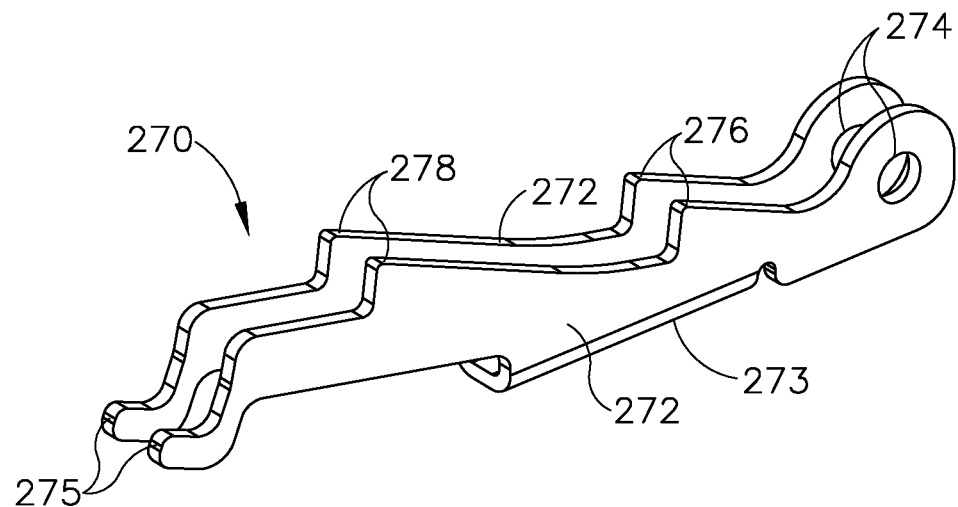
FIG. 19 depicts a perspective view of a dual lockout lever of the distal lockout mechanism of the surgical stapler of FIG. 1A.
Figure 20:
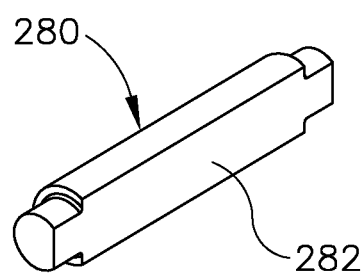
FIG. 20 depicts a perspective view of a stop member of the distal lockout mechanism of the surgical stapler of FIG. 1A.

As shown in FIGS. 18-20, distal lockout lever (270) of the present example is configured as a dual-sided structure having first and second lateral sides (272) that are spaced apart from one another and parallel to one another, and a lower bridge (273) that interconnects proximal portions of sides (272) along their lower edges. A proximal end of lockout lever (270) includes a pair of openings (274) configured to receive a pivot pin (279) therethrough, and a distal end of lockout lever (270) includes a pair of distally extending tabs (275). Along its medial portion, lockout lever (270)

further includes a proximal pair of lockout teeth (276) extending upwardly from lever sides (272), and a distal pair of lockout teeth (278) extending upwardly from lever sides (272) and spaced distally from proximal lockout teeth (276). As described below, lockout teeth (276, 278) are configured to engage a proximally facing flat face (282) of fixed pin (280) to establish lockout positions that prevent closure and firing of end effector (16) in the absence of an unspent staple cartridge unit (160).

As shown in FIGS. 18 and 3, lever pivot pin (279) extends laterally through proximal openings (274) of distal lockout lever (270), a corresponding pair of openings (67) formed in a distal portion of staple bar (60) (see FIG. 3), and a corresponding slot (77) formed in a distal portion of knife bar (70) (see FIG. 3). Accordingly, distal lockout lever (270) is longitudinally fixed yet rotatable relative to staple bar (60), while slot (77) permits knife bar (70) to translate longitudinally relative to staple bar (60) and distal lockout lever (270) to actuate knife member (194) of staple cartridge unit (160) independently of staple driver member (186), in the manner described above. As also shown in FIGS. 18 and 3, fixed pin (280) extends laterally through an elongate slot (79) formed in the distal portion of knife bar (70), and a corresponding pair of elongate slots (69) formed in the distal portion of staple bar (60). As described above, the opposed lateral ends of fixed pin (280) are fixed within distal jaw portions (46) of stapler side plates (40). Accordingly, elongate slots (69, 79) enable staple bar (60) and knife bar (70) to translate longitudinally, with distal lockout lever (270), relative to fixed pin (280) to effect closure and firing of end effector (16) loaded with an unspent staple cartridge unit (160).

Figure 21:
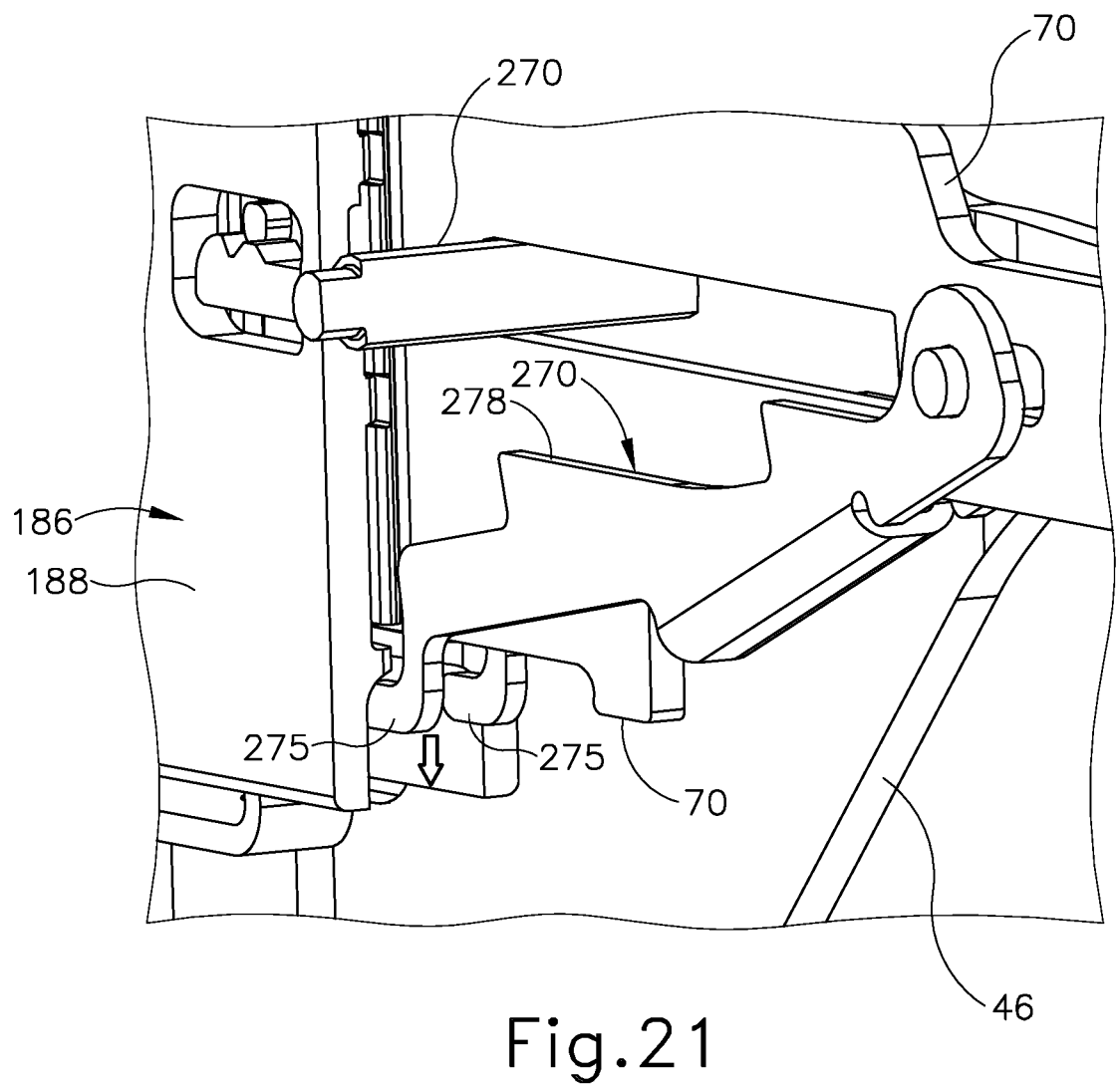
FIG. 21 depicts an enlarged perspective view of the dual lockout lever of the distal lockout mechanism of the surgical stapler of FIG. 1A being driven from a first lockout position to a bypass position by a staple driver member of an unspent staple cartridge unit loaded into the end effector.
Figure 22A:
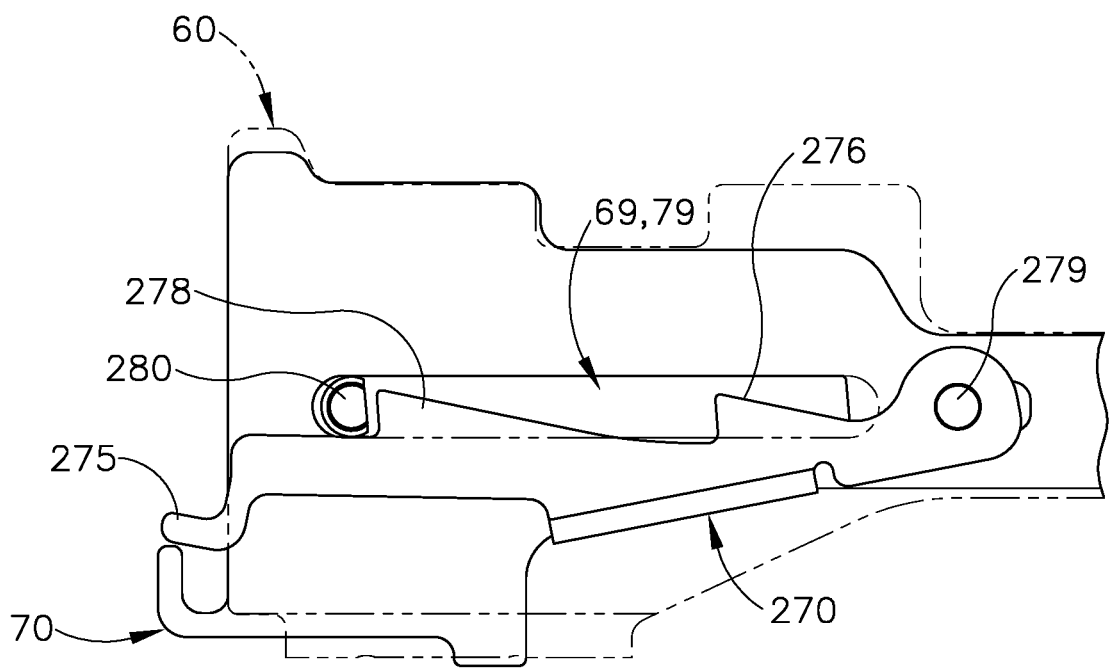
FIG. 22A depicts a side elevational view of a distal portion of the firing system and the distal lockout mechanism of the surgical stapler of FIG. 1A, showing the dual lockout lever in a first lockout position in which the dual lockout lever inhibits distal actuation of the closure system to prevent closure of the end effector in the absence of an unspent staple cartridge unit in the end effector.
Figure 22B:
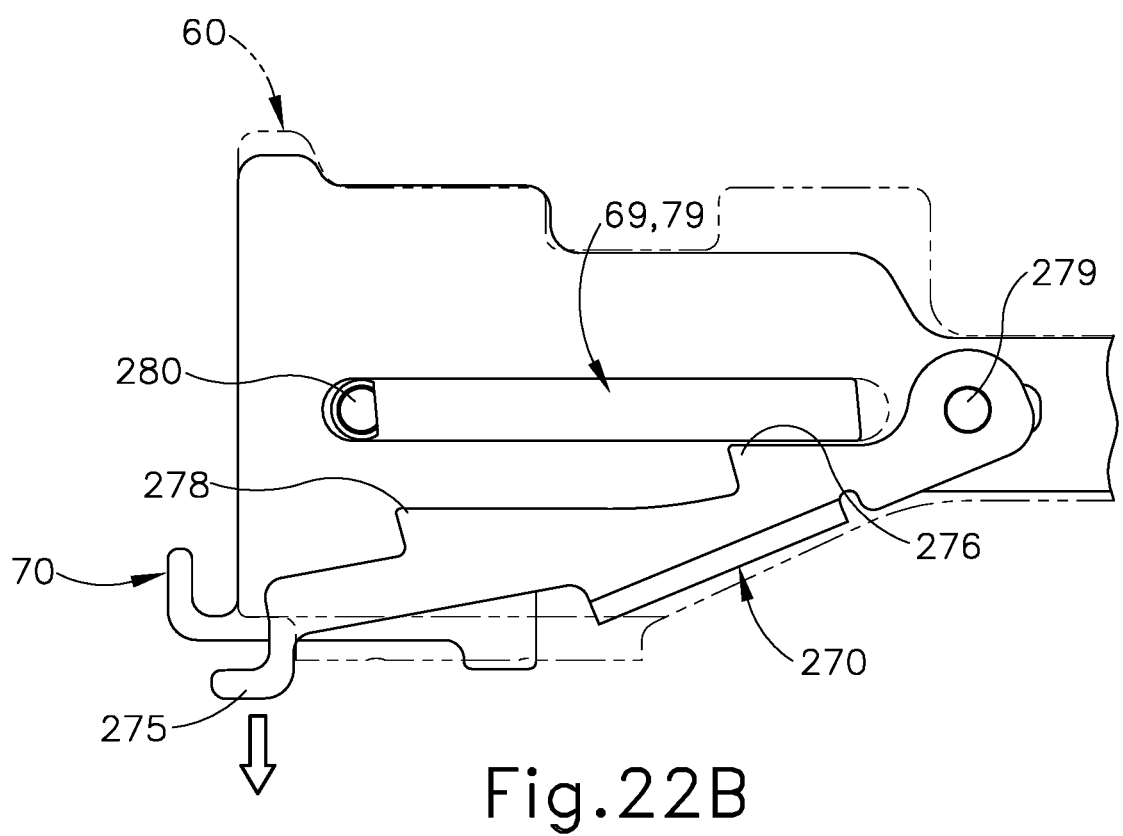
FIG. 22B depicts a side elevational view of a distal portion of the firing system and the distal lockout mechanism of the surgical stapler of FIG. 1A, showing the dual lockout lever pivoted to a bypass position in which the dual lockout lever permits distal actuation of the closure system and the firing system for closure and firing of the end effector when loaded with an unspent staple cartridge unit.
Figure 22C:
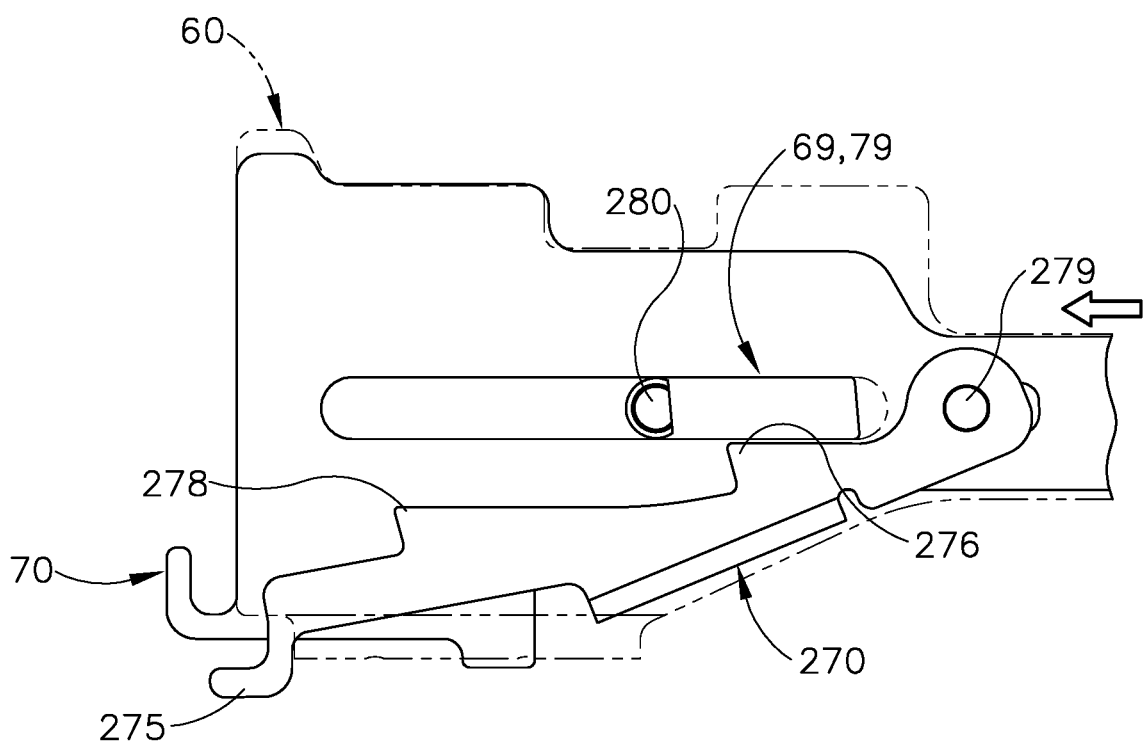
FIG. 22C depicts a side elevational view of a distal portion of the firing system and the distal lockout mechanism of the surgical stapler of FIG. 1A, showing the firing system and the dual lockout lever actuated distally during closure of the end effector.
Figure 22D:
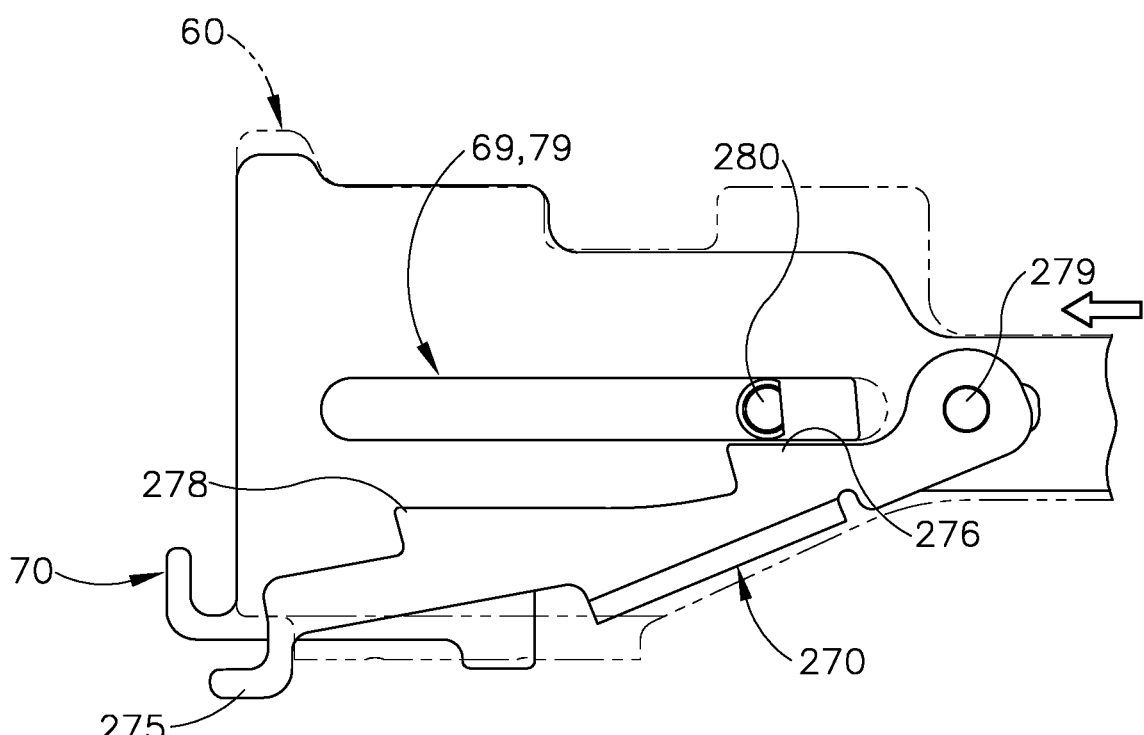
FIG. 22D depicts a side elevational view of a distal portion of the firing system and the distal lockout mechanism of the surgical stapler of FIG. 1A, showing the firing system and the dual lockout lever actuated further distally during firing of the end effector.
Figure 22E:
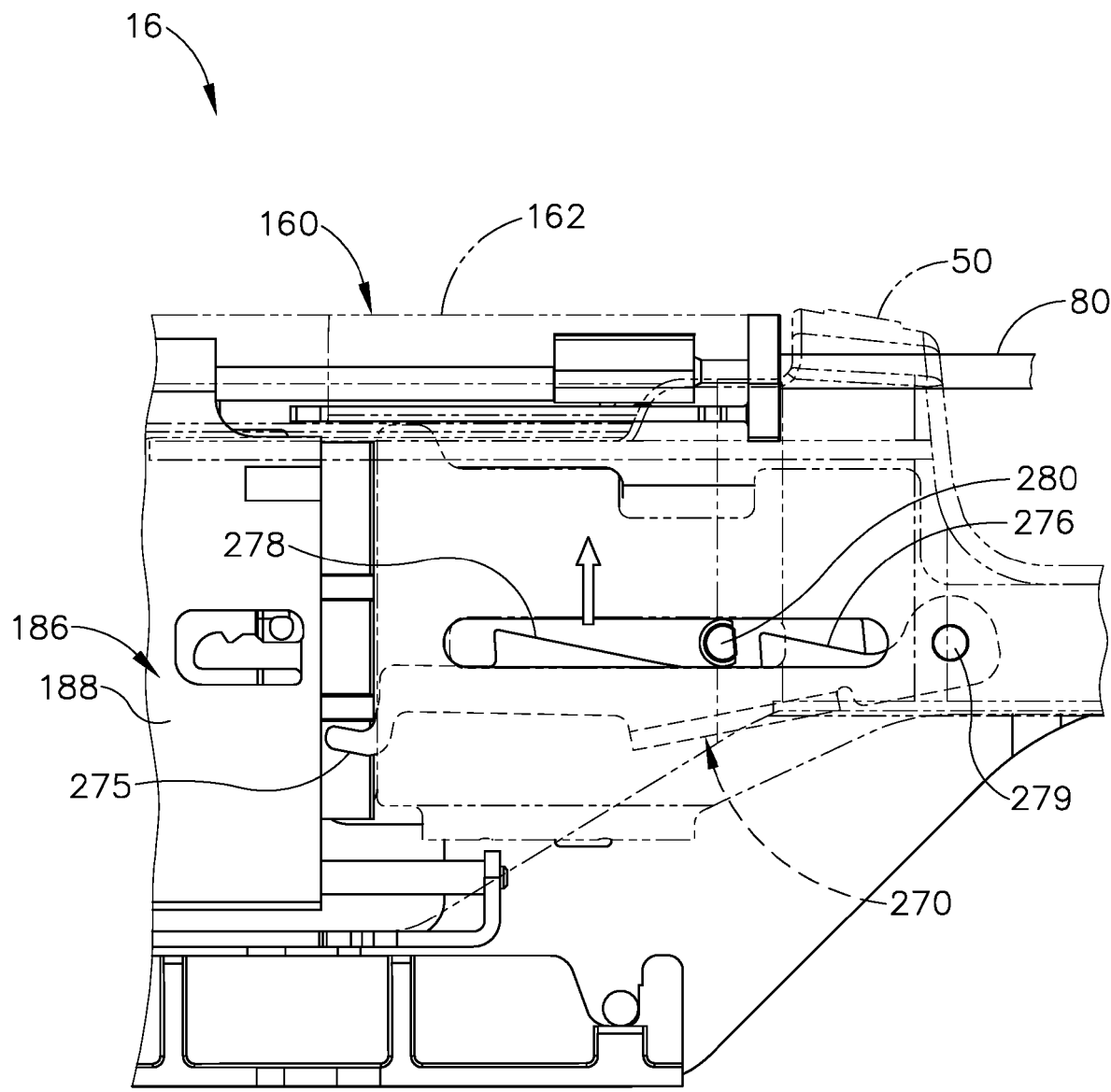
FIG. 22E depicts an enlarged side elevational view of the end effector of the surgical stapler of FIG. 1A, showing the dual lockout lever pivoting to a second lockout position after the end effector is fired so that the dual lockout lever inhibits further firing of the end effector with the now spent staple cartridge unit.

As shown in FIGS. 21-22E, distal lockout lever (270) is configured to pivot relative to staple bar (60) and knife bar (70) between a generally horizontal, raised position in which proximal lockout teeth (276) or distal lockout teeth (278) are configured to engage fixed pin (280), and a lowered position in which lockout teeth (276, 278) are configured to bypass fixed pin (280). Distal lockout lever (270) may be biased toward the raised position by any suitable biasing element, such as a resilient member (not shown).

FIG. 22A shows distal lockout lever (270) in a first raised lockout position that distal lockout lever (270) is configured to assume and maintain when end effector (16) is in an open state (i.e., when closure system (22) and firing system (24) are unactuated), and when an unspent staple cartridge unit (160) is absent from end effector (16); for example, when a staple cartridge unit (160) is entirely absent from end effector (16), or when end effector (16) is loaded with a spent staple cartridge unit (160). In this first raised lockout position, distal lockout teeth (278) are positioned to engage flat face (282) of fixed pin (280), thereby inhibiting distal actuation of firing system (24). Because firing system (24) is operatively coupled with closure system (22) in the manner described above, this locking of firing system (24) in its unactuated state also inhibits actuation of closure system (22), such that end effector (16) is locked in an open state.

As shown in FIGS. 21 and 22B, loading of an unspent staple cartridge unit (160) into end effector (16) is configured to pivot distal lockout lever (270) into its lowered bypass position. Specifically, staple driver member (186) of an unspent staple cartridge unit (160) is positioned proximally within cartridge housing (162) such that proximal base portion (188) of staple driver member (186) is configured to drive distally extending tabs (275) of distal lockout lever (270) downwardly as unspent staple cartridge unit (160) is seated into distal support structure (48) of end effector (16). This engagement forces distal lockout lever (270) to pivot downwardly from its first raised lockout position (FIG. 22A) to a lowered bypass position (FIG. 22B).

As shown in FIG. 22C, with distal lockout lever (270) in the lowered bypass position, staple bar (60) and knife bar (70) of firing system (24) are permitted to actuate distally with closure bar (50) in response to squeezing of closure trigger (36) by the operator. In this manner, as shown in FIGS. 1B-1C described above, end effector (16) is closed to clamp tissue between anvil (210) and cartridge deck (164) of unspent staple cartridge unit (160). As shown in FIG. 22D, with distal lockout lever (270) remaining in the lowered bypass position, staple bar (60) and knife bar (70) are driven further distally relative to closure bar (50) through a firing stroke in response to squeezing of firing trigger (38), thus firing end effector (16) with unspent staple cartridge unit (160) to staple and cut the clamped tissue.

FIG. 22E shows end effector (16) after completion of the firing stroke on staple cartridge unit (160), such that staple cartridge unit (160) is now spent. As described above in connection with FIG. 7, stapling detent features (185, 189) maintain staple driver member (186) in a distal position within cartridge housing (162) after staple cartridge unit (160) is fired. Accordingly, as staple bar (60) and knife bar (70) retract proximally in response to the operator releasing firing trigger (38), distally extending tabs (275) of distal lockout lever (270) disengage proximal base portion (188) of staple driver member (186). Consequently, via bias imparted by a biasing member, distal lockout lever (270) automatically pivots upwardly to assume a second raised lockout position, as shown in FIG. 22E. In the second raised lockout position, proximal lockout teeth (276) are positioned to engage proximal flat face (282) of fixed pin (280) and thereby prevent further actuation of firing system (24) while end effector (16) remains clamped with the now-spent staple cartridge unit (160). In this manner, distal lockout lever (270) inhibits actuation of firing system (24) more than once with the same staple cartridge unit (160) while the end effector (16) remains clamped. Advantageously, this protects against inadvertent re-actuation of knife (198) in a manner that could cut through and compromise the established staple line after the staples (170) are formed in the clamped tissue. This functionality of distal lockout lever (270) thus reminds the operator that the spent staple cartridge unit (160) must be replaced with another fresh, unspent staple cartridge unit (160) in order to perform another firing into tissue.

As described above, after firing end effector (16) and releasing firing trigger (38), the operator may depress release button (see FIGS. 1A-1D and 4A-4C) to return closure system (22) to the unactuated state and reopen end effector (16) to release the staple and cut tissue. As staple bar (60) and knife bar (70) retract proximally, distal lockout lever (270) ratchets proximally along the underside of fixed pin (280), thus returning distal lockout lever (270) to the first raised lockout position shown in FIG. 22A. Consequently, the operator is then prevented from re-closing end effector (16) while the spent staple cartridge unit (160) remains loaded. Accordingly, and advantageously, distal lockout lever (270) is operable as a dual-lockout member in that it is configured to inhibit actuation of both the closure system (22) and firing system (24) in the absence of an unspent staple cartridge unit (160). Moreover, distal lockout lever (270) is configured to cooperate with proximal firing lockout lever (140) described above to ensure safe use of surgical stapler (10).

Figure 23:
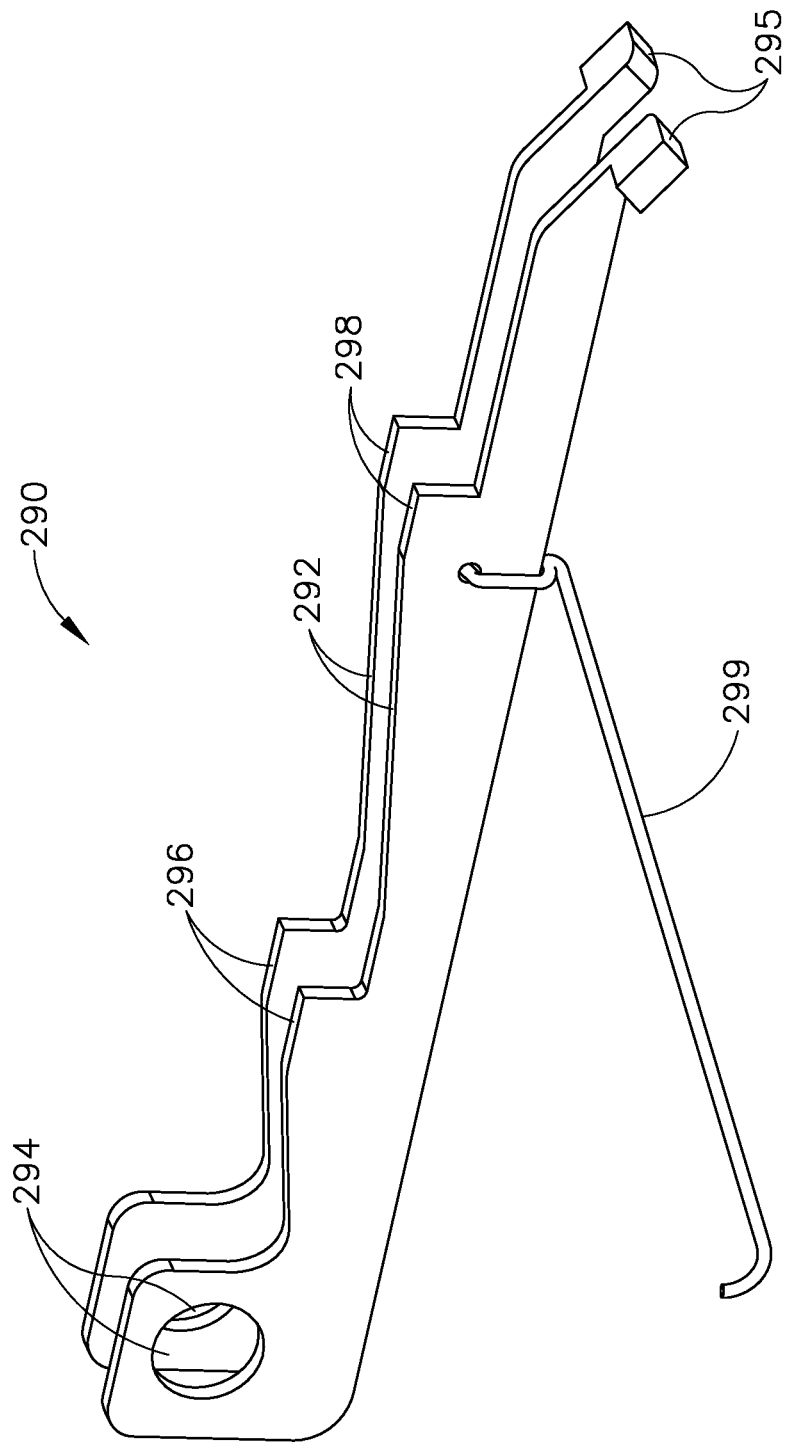
FIG. 23 depicts a perspective view of another exemplary dual lockout lever suitable for use with the distal lockout mechanism of the surgical stapler of FIG. 1A.

G. Exemplary Alternative Distal Lockout Lever Having Downwardly Sloping Distal Tabs FIG. 23 shows an exemplary alternative distal lockout lever (290) suitable for use with surgical stapler (10) in place of distal lockout lever (270) described above. Distal lockout lever (290) is similar to distal lockout lever (270) in that distal lockout lever (290) is configured as a dual-sided structure having first and second lateral sides (292) that are spaced apart from one another and parallel to one another. Furthermore, a distal lockout lever (290) includes a pair of openings (294) configured to receive a pivot pin (not shown) therethrough, and a distal end of lockout lever (290) includes a pair of distally extending tabs (295). Unlike distally extending tabs (275) of distal lockout lever (270), which slope upwardly, distal extending tabs (295) slope downwardly. Accordingly, distal lockout lever (290) may be suitable for use with other types of staple cartridge units of which a proximal end of the staple driver member is shaped differently than proximal base portion (188) of staple driver member (186) described above.

Similar to distal lockout lever (270), distal lockout lever (290) further includes a proximal pair of lockout teeth (296) extending upwardly from lever sides (292), and a distal pair of lockout teeth (298) extending upwardly from lever sides (292). Lockout teeth (296, 298) of distal lockout lever (290) are configured to cooperate with fixed distal pin (280) in a manner similar to lockout teeth (276, 278) of distal lockout lever (270) described above. Similar to lockout lever (270), lockout lever (290) is pivotable between a raised lockout position and a lowered bypass position. Lockout lever (290) is shown with a resilient member in the form of a leaf spring (299), which operates to resiliently bias lockout lever (290) toward a raised lockout position.

II. Exemplary Alternative Distal Lockout Mechanism

In some instances, it may be desirable to alternatively configure the distal lockout mechanism of surgical stapler end effector (16) such that lockout member (270) is mounted to closure bar (50) rather than to staple bar (60). FIGS. 24-28D illustrate a right-angle linear surgical stapler (310) having an exemplary alternative distal lockout mechanism with such a configuration. Surgical stapler (310) is otherwise similar to surgical stapler (10) except as otherwise described below. As described in greater detail, the distal lockout mechanism includes a movable lockout member (380) and a fixed stop member (390) that are operable in a manner similar to movable lockout member (270) and stop member (280) of surgical stapler (10) described above. In particular, lockout member (380) and stop member (390) are configured to cooperate to inhibit closure of end effector (316) when an unspent staple cartridge unit (460) is absent from end effector (316), and to inhibit firing of end effector (316) more than once with the same staple cartridge unit (460). Surgical stapler (310) is similar to surgical stapler (10) described above except as otherwise described below.

Figure 24:
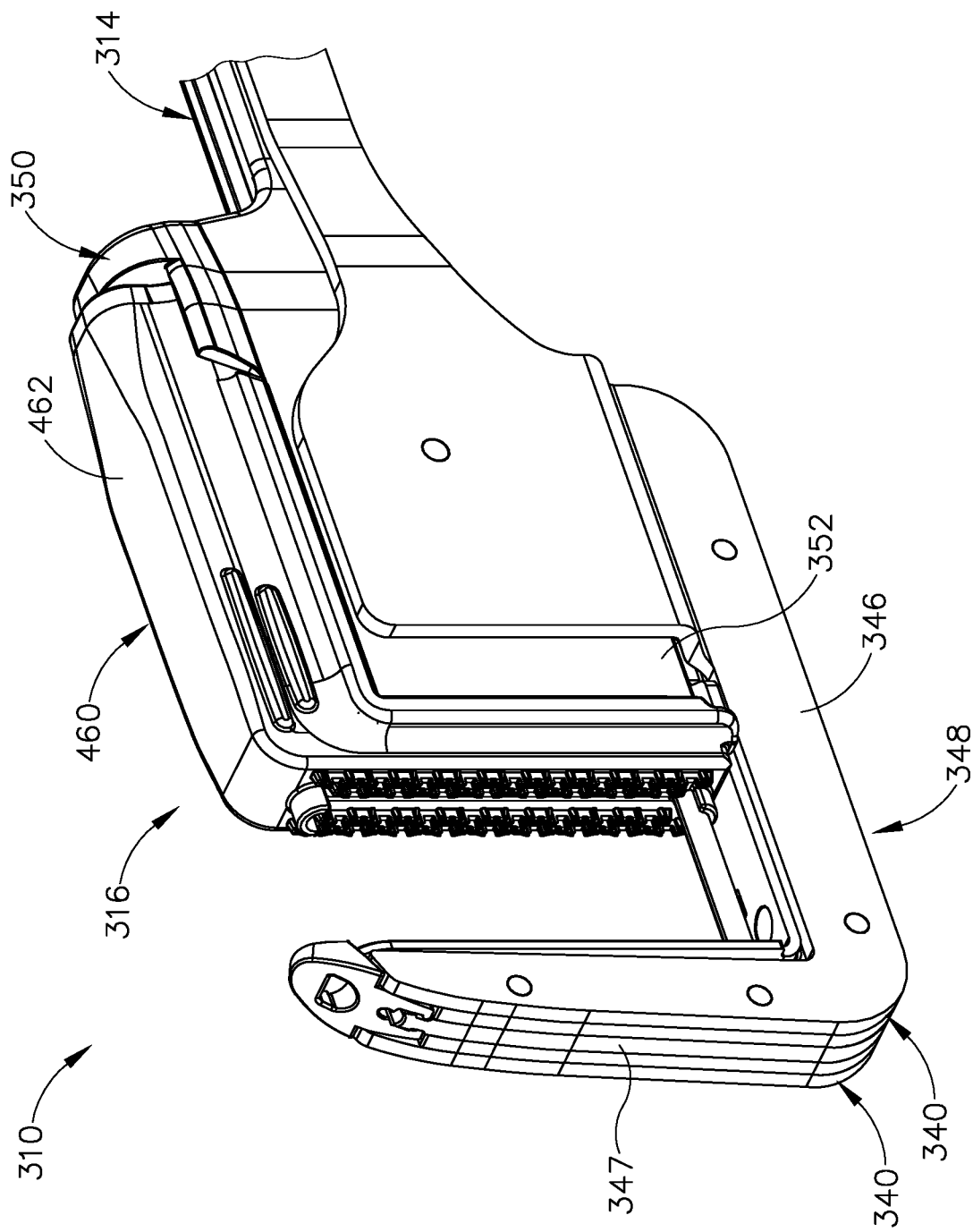
FIG. 24 depicts a perspective view of an end effector of another exemplary surgical stapler having a distal lockout mechanism operable to inhibit actuation of the closure system and the firing system of the surgical stapler.
Figure 25:
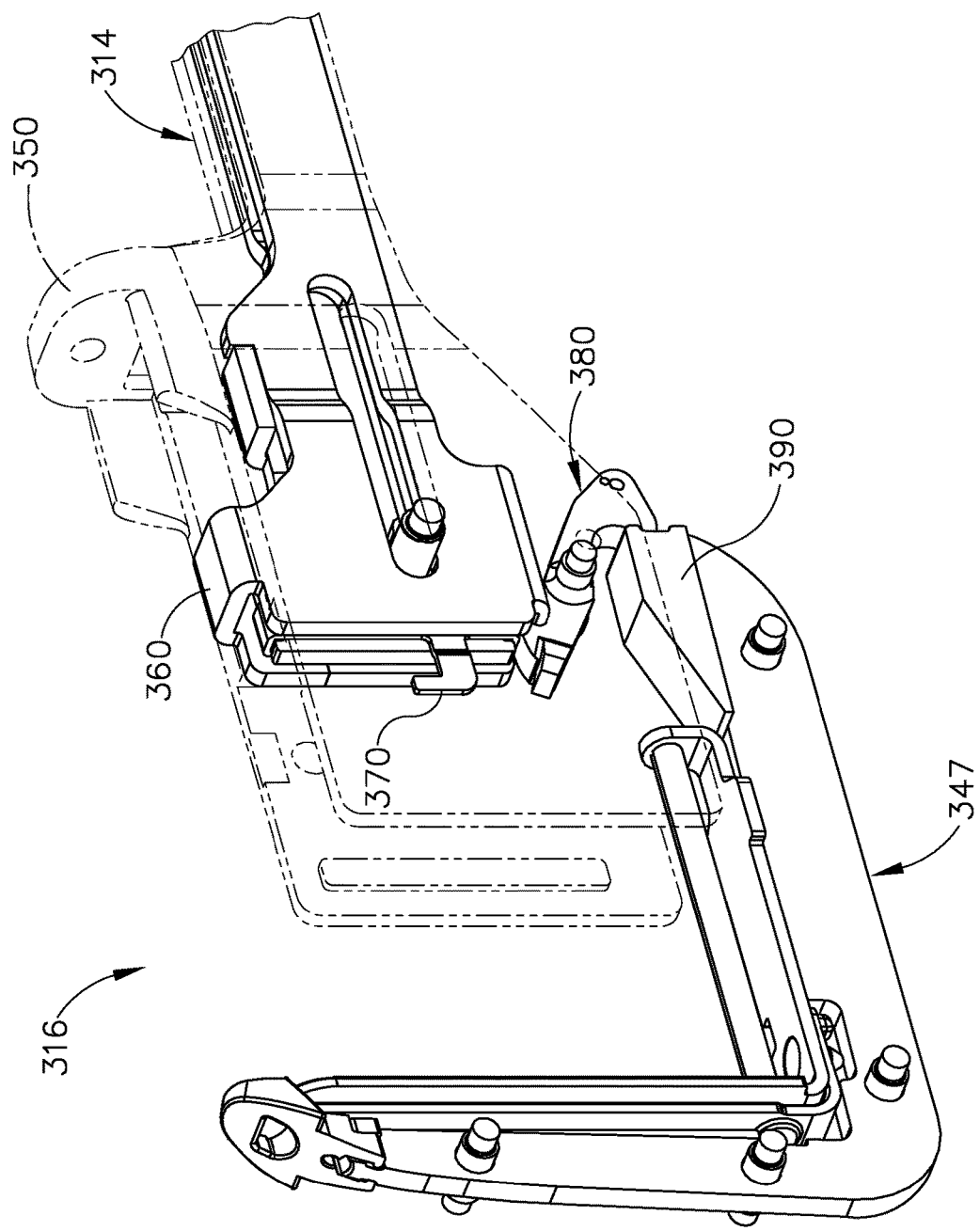
FIG. 25 depicts a perspective view of the end effector of the surgical stapler of FIG. 24, with various components omitted for clarity, showing a dual lockout lever and a stop member of the distal lockout mechanism.

As shown in FIGS. 24 and 25, surgical stapler (310) includes a shaft assembly (314) that extends distally from a handle assembly (not shown), and an end effector (316) at a distal end of shaft assembly (314). Surgical stapler (310) further includes a pair of longitudinally extending side plates (340) each having a distal jaw portion (346), and an inner jaw member (347) positioned laterally between distal jaw portions (346). A closure system of surgical stapler (310) includes an elongate closure bar (350) slidably disposed between stapler side plates (340). A firing system of surgical stapler (310) includes an elongate actuatable staple bar (360) slidably nested within closure bar (350), and an elongate actuatable knife bar (370) slidably nested within staple bar (360). A cartridge-receiving distal portion (352) of closure bar (350) cooperates with distal jaw portions (346) of stapler side plates (340) and inner jaw member (347) to define a U-shaped distal support structure (348) of end effector (316). As shown in FIG. 24, distal support structure (348) is configured to receive a staple cartridge unit (460) therein, which may be similar to staple cartridge unit (160) described above.

Figure 26:
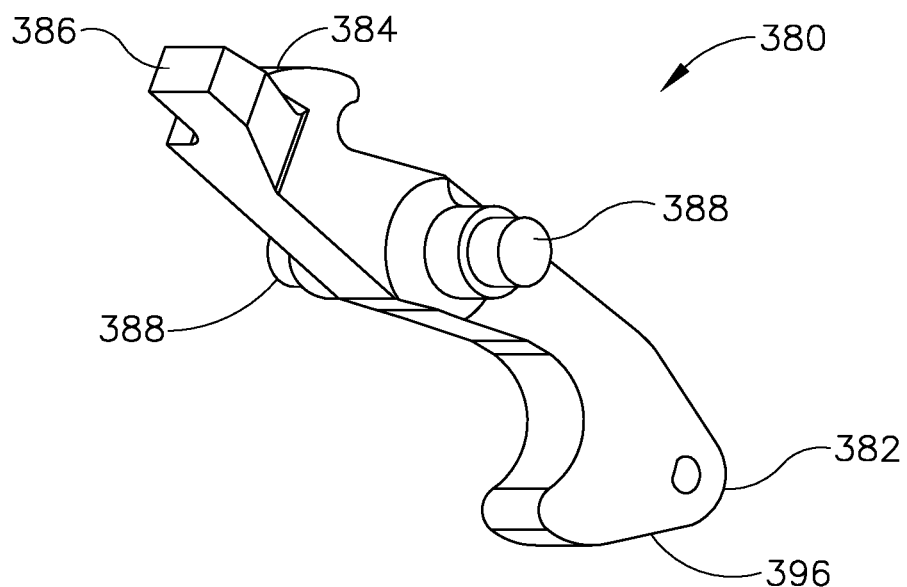
FIG. 26 depicts a perspective view of the dual lockout lever of the distal lockout mechanism of the surgical stapler of FIG. 24.
Figure 27:
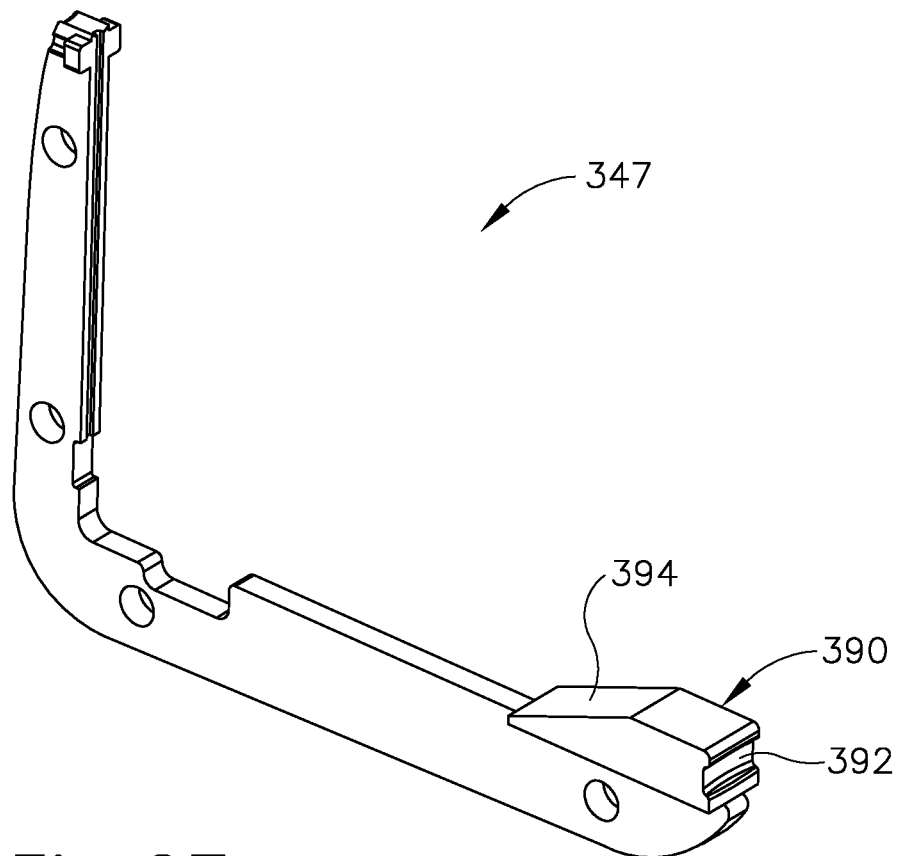
FIG. 27 depicts a perspective view of the stop member of the distal lockout mechanism of the surgical stapler of FIG. 24.

As shown in FIGS. 25-27, the distal lockout mechanism of surgical stapler (310) includes a movable lockout member in the form of lockout lever (380) pivotably mounted to cartridge-receiving distal portion (352) of closure bar (350), and a fixed stop member in the form of proximally-facing lug (390) affixed to a proximal end of inner jaw member (347). As shown in FIG. 26, distal lockout lever (380) includes a first lockout feature in the form of a proximal hook (382) at a proximal end of lockout lever (380), and a second lockout feature in the form of a distal hook (384) at a distal end of lockout lever (380). A tab (386) projects distally from distal hook (384) and is configured to be engaged by the proximal end of a staple driver member (486) of staple cartridge unit (460) to pivot lockout lever (380) between a lockout position (see, e.g., FIGS. 28A and 28D) and a bypass position (see, e.g., FIGS. 28B and 28C). Lockout lever (380) further includes a pair of pivot posts (388) that extend laterally outward from opposed lateral sides of lockout lever (380) at a mid-point of lockout lever (380) between proximal hook (382) and distal hook (384). Pivot posts (388) are rotatably received within corresponding openings formed in opposed lateral sides of cartridge-receiving distal portion (352) of closure bar (350), thus pivotably mounting lockout lever (380) to closure bar (350) about a lateral pivot axis.

As shown in FIGS. 28A-28D, lockout lever (380) is configured to pivot about pivot posts (388) between an angled position in which lockout lever (380) is configured to inhibit actuation of the closure system and/or the firing system of surgical stapler (310); and a generally horizontal bypass position in which lockout lever (380) is configured to permit actuation of the closure and firing systems of stapler (310) to permit closure and firing of end effector (316) loaded with an unspent staple cartridge unit (460). Lockout lever (380) of the present example is biased toward the angled position by a biasing member of any suitable type, such as a resilient member similar to leaf spring (299) described above.

Figure 28A:
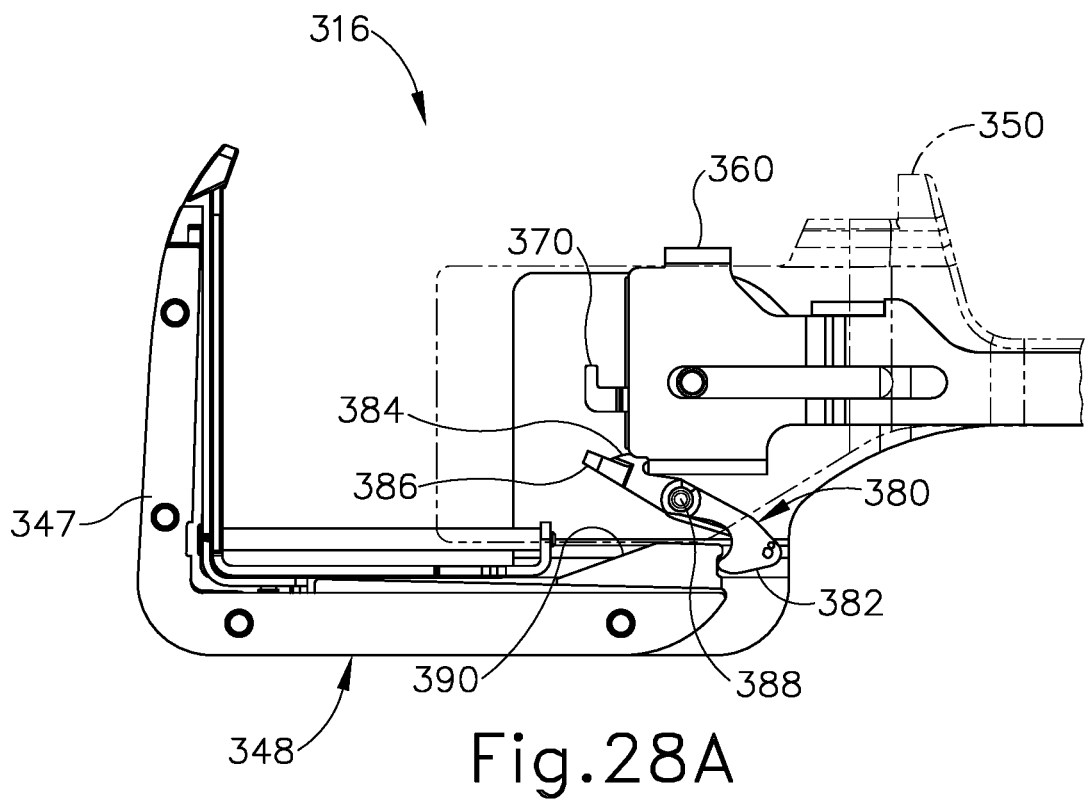
FIG. 28A depicts a side elevational view of the end effector of the surgical stapler of FIG. 24, with various components omitted for clarity, showing the end effector in an open state and with the dual lockout lever in a first lockout position in which it engages the stop member to prevent closure of the end effector in the absence of an unspent staple cartridge unit.

FIGS. 25 and 28A show distal lockout lever (380) in a first angled lockout position that distal lockout lever (380) is configured to assume and maintain when end effector (316) is in an open state (i.e., when the closure system and firing system are unactuated), and when an unspent staple cartridge unit (460) is absent from end effector (316); for example, when a staple cartridge unit (460) is entirely absent from end effector (316), or when end effector (316) is loaded with a spent staple cartridge unit (460). In this first angled lockout position, distal hook (384) captures the distal ends of staple bar (360) and knife bar, while proximal hook (382) captures a proximal end of lug (390). As seen in FIG. 27, the proximal end of lug (390) includes a groove (392) that is configured to receive proximal hook (382) of distal lockout lever (380) in the first angled lockout position. This simultaneous engagement of distal lockout lever (380) with lug (390) and staple bar (360) in the absence of an unspent staple cartridge unit (460) in end effector (316) inhibits distal actuation of both the closure system and the firing system of surgical stapler (310), thus preventing closure of end effector (316). Specifically, proximal hook (382) grounds closure bar (350) longitudinally to stapler side plates (340) and inner jaw member (347), and distal hook (384) grounds staple bar (360) and knife bar (370) longitudinally to closure bar (350).

Figure 28B:
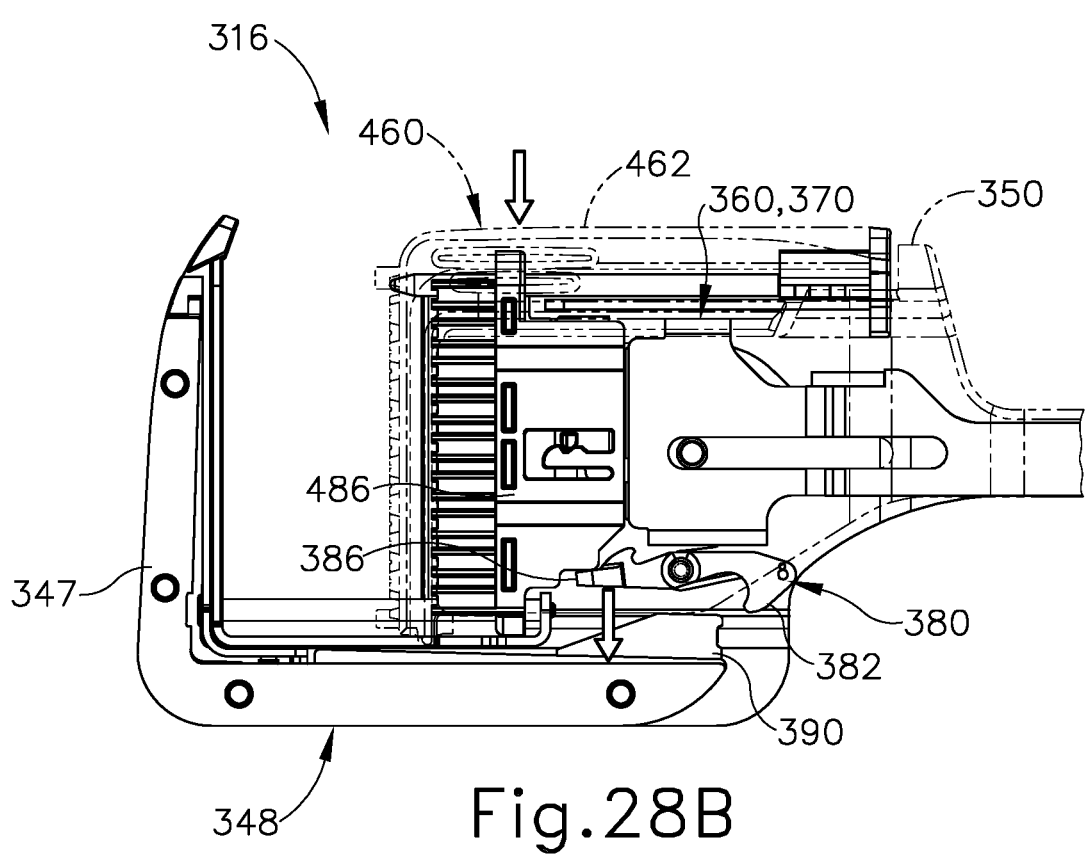
FIG. 28B depicts a side elevational view of the end effector of the surgical stapler of FIG. 24, with various components omitted for clarity, showing an unspent staple cartridge unit loaded into the end effector and thereby pivoting the dual lockout lever from the first lockout position to a bypass position that permits closure and firing of the end effector.

As shown in FIG. 28B, loading of an unspent staple cartridge unit (460) into end effector (316) causes distal lockout lever (380) to pivot from the first lockout position to a horizontal bypass position. Specifically, a proximal end of staple driver member (486) of unspent staple cartridge unit (460) engages and drives distal tab (386) of lockout lever (380) downwardly. This forces lockout lever (380) to pivot to a horizontal position such that proximal hook (382) disengages lug (390) and distal hook (384) disengages staple bar (360).

Figure 28C:
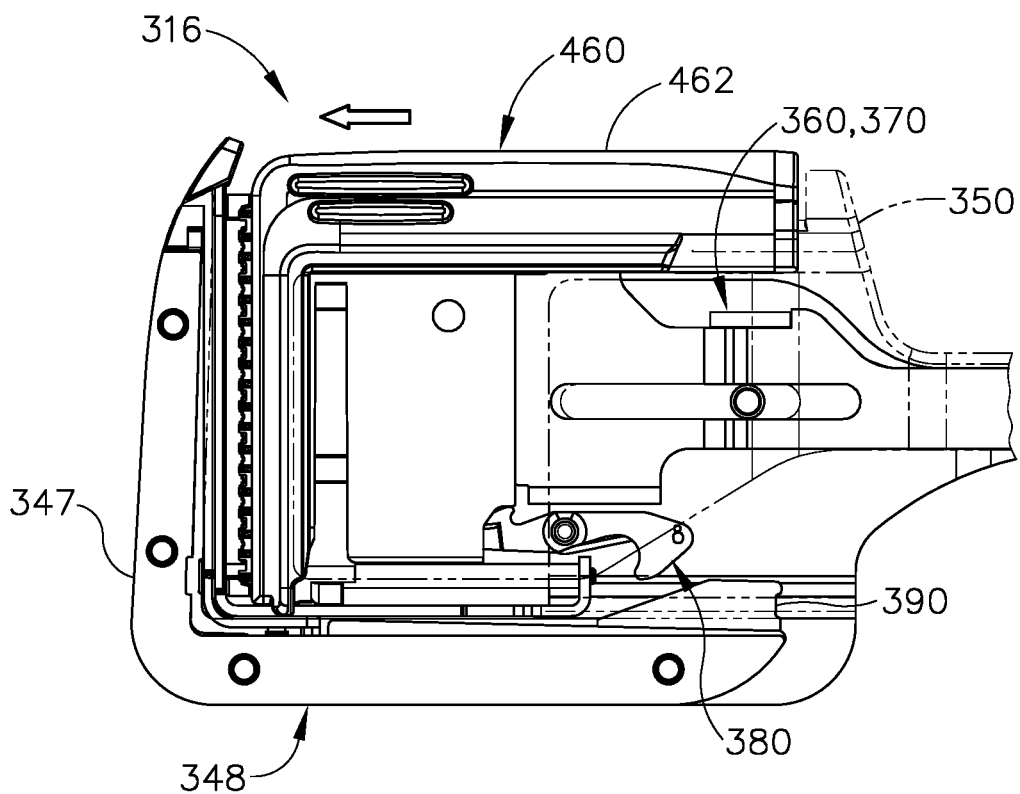
FIG. 28C depicts a side elevational view of the end effector of the surgical stapler of FIG. 24, with various components omitted for clarity, showing the end effector actuated to a closed state by the closure system while the dual lockout lever remains in the bypass position.

As shown in FIG. 28C with distal lockout lever (380) now in the horizontal bypass position, closure bar (350), staple bar (360), and knife bar (370) are free to actuate distally relative to stapler side plates (340) to close end effector (316) and thereby clamp tissue. As shown, distal lockout lever (380) translates with closure bar (350) such that proximal hook (382) translates distally beyond the proximal face of lug (390). Additionally, once end effector (316) is fully closed, staple bar (360) and knife bar (370) are free to actuate further distally relative to closure bar (350) through a firing stroke to fire end effector (316) with unspent staple cartridge unit (460), thereby stapling and cutting the clamped tissue.

Figure 28D:
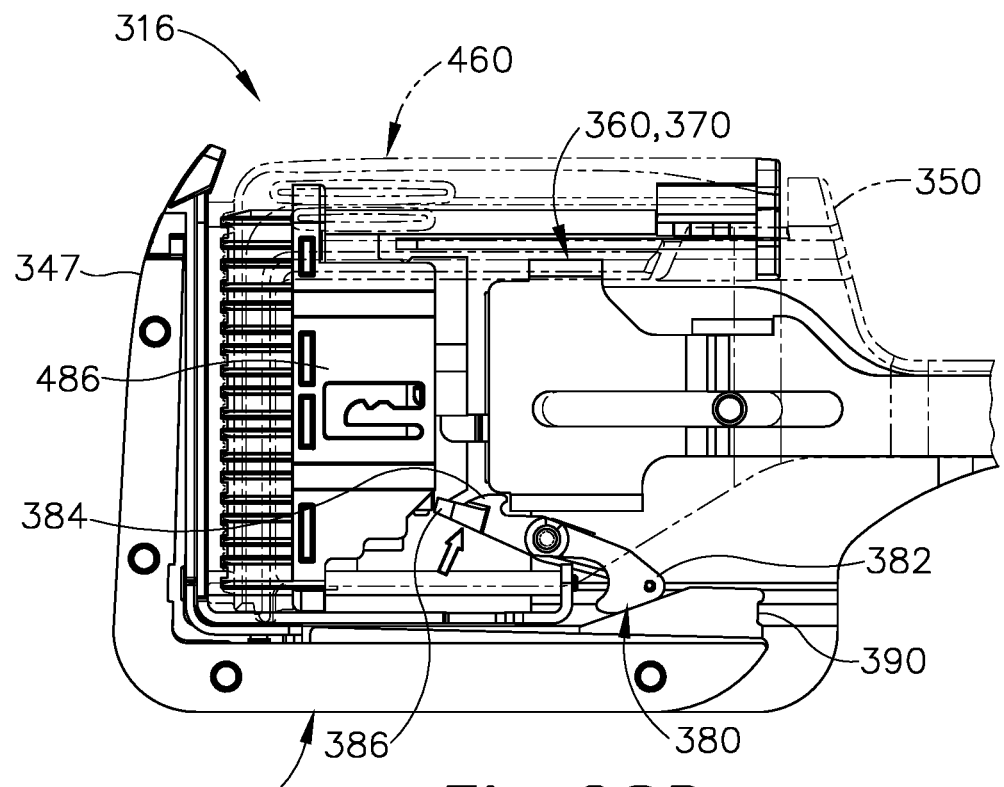
FIG. 28D depicts a side elevational view of the end effector of the surgical stapler of FIG. 24, with various components omitted for clarity, showing the dual lockout lever pivoting to a second lockout position after the end effector is fired so that the dual lockout lever inhibits further firing of the end effector with the now spent staple cartridge unit.

FIG. 28D shows end effector (316) after completion of a firing stroke on staple cartridge unit (460), such that staple cartridge unit (460) is now spent. Similar to staple driver member (186) of staple cartridge unit (160), staple driver member (486) of cartridge unit (460) is configured to remain in a distal position within cartridge housing (462) upon completion of the firing stroke. Accordingly, as staple bar (360) and knife bar (370) retract proximally in response to the operator releasing the firing trigger (not shown) of surgical stapler (310), distal tab (386) of distal lockout lever (380) disengages the proximal end of staple driver member (486). Consequently, via bias imparted by a biasing member, distal lockout lever (380) automatically pivots relative to closure bar (350) to assume a second angled lockout position, as shown in FIG. 22D. In the second angled lockout position, distal hook (384) of lockout lever (380) captures the distal ends of staple bar (360) and knife bar (370), thus inhibiting distal actuation of bars (360, 370) relative to closure bar (350) and preventing re-firing while end effector (316) remains clamped with the now-spent staple cartridge unit (460). Similar to the benefit provided in end effector (16), this functionality in end effector (316) protects against inadvertent re-actuation of a knife (not shown) of staple cartridge unit (460) in a manner that could cut through and compromise the established staple line after staples have been formed in the clamped tissue.

Upon closure bar (350), staple bar (360), and knife bar (370) being retracted proximally and spent staple cartridge unit (460) being removed from end effector (316), distal lockout lever (380) is configured to automatically reassume the first angled lockout position shown in FIGS. 25 and 28A. In the present example, a distal end of lug (390) includes a first ramped surface (394) and a confronting side of proximal hook (382) of distal lockout lever (380) includes a second ramp surface (396). Ramp features are configured to cam against one another to pivot lockout lever (380) into the bypass position as bars (350, 360, 370) are retracted proximally, thus enabling distal lockout lever (380) to retract proximally with closure bar (350) and reassume the first angled lockout position until another fresh, unspent staple cartridge unit (460) is loaded into end effector (316).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a body; (b) a shaft assembly extending distally from the body; (c) an end effector at a distal end of the shaft assembly, wherein the end effector is actuatable between an open state for receiving tissue and a closed state for clamping the tissue, wherein the end effector is configured to receive a staple cartridge having staples; (d) a closure system operatively coupled with the end effector, wherein the closure system is operable to actuate the end effector from the open state to the closed state; (e) a firing system operatively coupled with the end effector, wherein the firing system is actuatable to fire the end effector and thereby staple and cut the clamped tissue; and (f) a lockout member operatively coupled with the closure system and the firing system, wherein the lockout member is configured to inhibit actuation of the closure system to prevent closure of the end effector when an unspent staple cartridge is absent from the end effector, wherein the lockout member is further configured to inhibit actuation of the firing system to prevent repeated firing of the end effector with the same staple cartridge.

Example 2

The surgical stapler of Example 1, wherein the end effector is configured to clamp and staple tissue in a plane that extends transversely to a longitudinal axis of the shaft assembly, wherein the surgical stapler is configured for use in an open surgical procedure.

Example 3

The surgical stapler of any of the preceding Examples, wherein the end effector includes a knife, wherein the lockout member is configured to prevent distal actuation of the knife following an initial firing of the end effector with the staple cartridge.

Example 4

The surgical stapler of any of the preceding Examples, wherein the lockout member is movable between a first position in which the lockout member is configured to inhibit actuation of the closure system and the firing system when an unspent staple cartridge is absent from the end effector, and a second position in which the lockout member is configured to permit actuation of the closure system and the firing system.

Example 5

The surgical stapler of any of Example 4, wherein the lockout member is resiliently biased toward the first position.

Example 6

The surgical stapler of any Examples 4 through 5, wherein the lockout member is configured to transition from the first position to the second position in response to an unspent staple cartridge being received by the end effector.

Example 7

The surgical stapler of Example 6, where the staple cartridge includes a staple driver member configured to eject the staples from the staple cartridge in response to actuation of the firing system, wherein the lockout member includes a projection configured to be engaged by the staple driver member when the unspent staple cartridge is first received by the end effector, wherein the engagement is configured to drive the lockout member from the first position to the second position.

Example 8

The surgical stapler of any of Examples 6 through 7, wherein when the unspent staple cartridge is seated within the end effector, the lockout member is configured to translate distally with the closure system while maintaining the second position.

Example 9

The surgical stapler of any of Examples 6 through 8, wherein the lockout member is configured to automatically return to the first position from the second position after the end effector is fired with the unspent staple cartridge.

Example 10

The surgical stapler of Examples 4 through 9, wherein the lockout member comprises a lever configured to pivot between the first position and the second position.

Example 11

The surgical stapler of Example 10, wherein the shaft assembly extends along a longitudinal axis, wherein the lever is configured to pivot about a lateral axis that extends transversely to the longitudinal axis.

Example 12

The surgical stapler of any of the preceding Examples, wherein the lockout member is configured to translate distally with the closure system relative to the body as the closure system actuates the end effector from the open state to the closed state.

Example 13

The surgical stapler of any of Example 12, further comprising a stop member that is fixed longitudinally relative to the body, wherein the lockout member is configured to engage the stop member to inhibit distal actuation of the closure system when an unspent staple cartridge is absent from the end effector in the open state.

Example 14

The surgical stapler of any of the preceding Examples, wherein the lockout member includes: (i) a first lockout feature operable to inhibit actuation of the closure system to prevent closure of the end effector when an unspent staple cartridge is absent from the end effector, and (ii) a second lockout feature operable to inhibit actuation of the firing system to prevent repeated firing of the end effector with the same staple cartridge.

Example 15

The surgical stapler of Example 14, wherein the first and second lockout features are spaced apart longitudinally along a longitudinal axis of the shaft assembly.

Example 16

A surgical stapler comprising: (a) a body; (b) a shaft assembly extending distally from the body; (c) an end effector at a distal end of the shaft assembly, wherein the end effector is actuatable between an open state for receiving tissue and a closed state for clamping the tissue, wherein the end effector is configured to receive a staple cartridge having staples; (d) a closure system operatively coupled with the end effector, wherein the closure system is operable to actuate the end effector from the open state to the closed state; (e) a firing system operatively coupled with the end effector, wherein the firing system is actuatable distally through a firing stroke to eject staples from the staple cartridge into the clamped tissue; and (f) a lockout member operatively coupled with the closure system and the firing system, wherein the lockout member includes: (i) a first lockout feature operable to inhibit actuation of the closure system when an unspent staple cartridge is absent from the end effector, and (ii) a second lockout feature operable to inhibit repeated actuation of the firing system through multiple firing strokes with the same staple cartridge.

Example 17

The surgical stapler of Example 16, wherein the first and second lockout features are spaced apart along a length of the lockout member.

Example 18

The surgical stapler of any of Examples 16 through 17, wherein the first lockout feature comprises a first projection, wherein the second lockout feature comprises a second projection.

Example 19

A surgical stapler comprising: (a) a body; (b) a shaft assembly extending distally from the body; (c) an end effector at a distal end of the shaft assembly, wherein the end effector is actuatable between an open state for receiving tissue and a closed state for clamping the tissue, wherein the end effector is configured to receive a staple cartridge having staples; (d) a closure system operatively coupled with the end effector, wherein the closure system is operable to actuate the end effector from the open state to the closed state; (e) a firing system operatively coupled with the end effector, wherein the firing system is actuatable distally through a firing stroke to eject staples from the staple cartridge into the clamped tissue; and (f) a lockout lever operatively coupled with the closure system and the firing system, wherein the lockout lever is pivotable between a first position in which the lockout lever is configured to inhibit actuation of the closure system and the firing system, and a second position in which the lockout lever is configured to permit actuation of the closure system and the firing system.

Example 20

The surgical stapler of Example 19, wherein the lockout lever is disposed within the end effector.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. patent application Ser. No. 16/395,357, entitled "Tissue Cutting Washer for Right Angle Surgical Stapler," filed on Apr. 26, 2019, issued as U.S. Pat. No. 11,266,403 on Mar. 8, 2022; U.S. patent application Ser. No. 16/395,358, entitled "Clamping Based Lockout Mechanism for Right Angle Surgical Stapler," filed on Apr. 26, 2019, issued as U.S. Pat. No. 11,202,629 on Dec. 21, 2021; and U.S. patent application Ser. No. 16/395,364, entitled "Staple Retainer for Right Angle Surgical Stapler," filed on Apr. 26, 2019, issued as U.S. Pat. No. 11,166,721 on Nov. 9, 2021 the disclosures of which are incorporated by reference above.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a shaft assembly;
   (b) an end effector at a distal end of the shaft assembly, wherein the end effector is actuatable between an open state for receiving tissue and a closed state for clamping the tissue, wherein the end effector is configured to receive a staple cartridge having staples;
   (c) a closure system operatively coupled with the end effector, wherein the closure system is operable to actuate the end effector from the open state to the closed state;
   (d) a firing system operatively coupled with the end effector, wherein the firing system is actuatable distally through a firing stroke to eject staples from the staple cartridge into the clamped tissue; and
   (e) a lockout member operatively coupled with the closure system and the firing system, wherein the lockout member includes:
      (i) a first lockout feature operable to inhibit actuation of the closure system to prevent closure of the end effector when an unspent staple cartridge is absent from the end effector, and
      (ii) a second lockout feature operable to inhibit repeated actuation of the firing system through multiple firing strokes with the same staple cartridge while the end effector is in the closed state.

2. The surgical stapler of claim 1, wherein the first and second lockout features are spaced apart along a length of the lockout member.

3. The surgical stapler of claim 1, wherein the first lockout feature comprises a first projection, wherein the second lockout feature comprises a second projection.

4. The surgical stapler of claim 1, wherein the end effector is configured to clamp and staple tissue in a plane that extends transversely to a longitudinal axis of the shaft assembly, wherein the surgical stapler is configured for use in an open surgical procedure.

5. The surgical stapler of claim 1, wherein the end effector includes a knife, wherein the lockout member is configured to prevent distal actuation of the knife following an initial firing of the end effector with the staple cartridge.

6. The surgical stapler of claim 1, wherein the lockout member is movable between a first position and a second position, wherein in the first position the first lockout feature is configured to inhibit actuation of the closure system and the second lockout feature is configured to inhibit actuation of the firing system, wherein in the second position the lockout member is configured to permit actuation of the closure system and the firing system.

7. The surgical stapler of claim 6, wherein the lockout member is resiliently biased toward the first position.

8. The surgical stapler of claim 7, wherein the lockout member is configured to transition from the first position to the second position in response to an unspent staple cartridge being received by the end effector.

9. The surgical stapler of claim 8, where the staple cartridge includes a staple driver member configured to eject the staples from the staple cartridge in response to actuation of the firing system, wherein the lockout member includes a projection configured to be engaged by the staple driver member when the unspent staple cartridge is first received by the end effector, wherein the engagement is configured to drive the lockout member from the first position to the second position.

10. The surgical stapler of claim 8, wherein when the unspent staple cartridge is seated within the end effector, the lockout member is configured to translate distally with the closure system while maintaining the second position.

11. The surgical stapler of claim 8, wherein the lockout member is configured to automatically return to the first position from the second position after the end effector is fired with the unspent staple cartridge.

12. The surgical stapler of claim 6, wherein the lockout member comprises a lever configured to pivot between the first position and the second position.

13. The surgical stapler of claim 12, wherein the shaft assembly extends along a longitudinal axis, wherein the lever is configured to pivot about a lateral axis that extends transversely to the longitudinal axis.

14. The surgical stapler of claim 1, wherein the lockout member is configured to translate distally with the closure system relative to a static portion of the shaft assembly as the closure system actuates the end effector from the open state to the closed state.

15. The surgical stapler of claim 14, further comprising a stop member that is fixed longitudinally relative to the static portion of the shaft assembly, wherein the lockout member is configured to engage the stop member to inhibit distal actuation of the closure system when an unspent staple cartridge is absent from the end effector in the open state.

16. A surgical stapler comprising:
   (a) a shaft assembly;
   (b) an end effector at a distal end of the shaft assembly, wherein the end effector is actuatable between an open state for receiving tissue and a closed state for clamping the tissue, wherein the end effector is configured to receive a staple cartridge having staples;
   (c) a closure system operatively coupled with the end effector, wherein the closure system is operable to actuate the end effector from the open state to the closed state;
   (d) a firing system operatively coupled with the end effector, wherein the firing system is actuatable distally through a firing stroke to eject staples from the staple cartridge into the clamped tissue; and
   (e) a lockout member operatively coupled with the closure system and the firing system, wherein the lockout member includes:
      (i) a first projection operable to inhibit actuation of the closure system to prevent closure of the end effector when an unspent staple cartridge is absent from the end effector, and
      (ii) a second projection operable to inhibit repeated actuation of the firing system through multiple firing strokes with the same staple cartridge while the end effector is in the closed state.

17. The surgical stapler of claim 16, wherein the lockout member is movable between a first position and a second position, wherein in the first position the first projection is configured to inhibit actuation of the closure system and the second projection is configured to inhibit actuation of the firing system, wherein in the second position the lockout member is configured to permit actuation of the closure system and the firing system.

18. The surgical stapler of claim 16, wherein the first projection comprises a first tooth, wherein the second projection comprises a second tooth spaced apart longitudinally from the first tooth.

19. A surgical stapler comprising:
(a) a shaft assembly;
(b) an end effector at a distal end of the shaft assembly, wherein the end effector is actuatable between an open state for receiving tissue and a closed state for clamping the tissue, wherein the end effector is configured to receive a staple cartridge having staples;
(c) a closure system operatively coupled with the end effector, wherein the closure system is operable to actuate the end effector from the open state to the closed state;
(d) a firing system operatively coupled with the end effector, wherein the firing system is actuatable distally through a firing stroke to eject staples from the staple cartridge into the clamped tissue;
(e) a first lockout feature operatively coupled with the closure system, wherein the first lockout feature is operable to inhibit actuation of the closure system to prevent closure of the end effector when an unspent staple cartridge is absent from the end effector; and
a second lockout feature operatively coupled with the firing system, wherein the second lockout feature is operable to inhibit repeated actuation of the firing system through multiple firing strokes with the same staple cartridge while the end effector is in the closed state.

20. The surgical stapler of claim 19, wherein the first and second lockout features are movable together relative to a static portion of the surgical stapler.

* * * * *